US009249184B2

(12) United States Patent
Robbins et al.

(10) Patent No.: US 9,249,184 B2
(45) Date of Patent: Feb. 2, 2016

(54) CARDIAC-SPECIFIC PROTEIN TARGETING DOMAIN

(75) Inventors: Paul David Robbins, Pittsburgh, PA (US); Maliha Zahid, Gibsonia, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 258 days.

(21) Appl. No.: 13/273,976

(22) Filed: Oct. 14, 2011

(65) Prior Publication Data

US 2012/0244136 A1  Sep. 27, 2012

Related U.S. Application Data

(60) Provisional application No. 61/393,278, filed on Oct. 14, 2010.

(51) Int. Cl.
| | |
|---|---|
| *C07K 7/06* | (2006.01) |
| *C07K 7/08* | (2006.01) |
| *A61K 38/00* | (2006.01) |

(52) U.S. Cl.
CPC ... *C07K 7/06* (2013.01); *C07K 7/08* (2013.01); *A61K 38/00* (2013.01); *C07K 2319/00* (2013.01); *C07K 2319/33* (2013.01)

(58) Field of Classification Search
CPC .................................... C07K 7/06; C07K 7/08
See application file for complete search history.

(56) References Cited

U.S. PATENT DOCUMENTS

| 5,911,983 A * | 6/1999 | Barranger et al. ......... 424/93.21 |
| 2002/0061299 A1 | 5/2002 | French |
| 2010/0221235 A1* | 9/2010 | Arranz ....................... 424/94.61 |
| 2010/0310495 A1 | 12/2010 | Schneider et al. |

FOREIGN PATENT DOCUMENTS

| WO | WO 2008/045976 | * | 4/2008 | ............. A61K 51/10 |
| WO | WO 2009/134962 | * | 11/2009 | ............. C07K 14/00 |
| WO | WO 2010/033868 | * | 3/2010 | ............. C07K 14/00 |
| WO | WO 2011/049449 | | 4/2011 | |

OTHER PUBLICATIONS

Zahid et al., Aug. 17, 2010, Identification of a Cardiac Specific Protein Transduction Domain by In Vivo Biopanning using a M13 Phage peptide Display Library in Mice, PLoS ONE, 5(8): 11 pages.*
Zahid, 2009, Targeting the Heart Using In Vivo Phage Display, University of Pittsburgh, Doctoral thesis, 132 pages.*
McGuire et al., 2004, In vitro selection of a peptide with high selectivity for cardiomyocytes in vivo, J Mol Biol, 342: 171-182.*
Lu et al., Aug. 2010, Targeting of Embryonic Stem Cells by Peptide-Conjugated Quantum Dots, PLoS ONE, 5(8): 10 pages.*
Arap et al., "Cancer Treatment by Targeted Drug Delivery to Tumor Vasculature in a Mouse Model", *Science*, 279(5349):377-380, Jan. 1998.
Bergmann et al., "Effect of NF-κ B Inhibition of TNF-α-Induced Apoptosis and Downstream Pathways in Cardiomyocytes", *Journal of Molecular and Cellular Cardiology*, 33(6):1223-1232, Jun. 2001.
Cavasin et al., "Gender Differences in Cardiac Function During Early Remodeling after Acute Myocardial Infarction in Mice", *Life Sciences*, 75(18):2181-2192, Sep. 2004.
Frantz et al., "Absence of NF-κB Subunit p50 Improves Heart Failure after Myocardial Infarction", *The FASEB Journal*, 20(11):1918-1920, Sep. 2006.
Htun et al., "Intramyocardial Infusion of FGF-1 Mimics Ischemic Preconditioning in Pig Myocardium", *Journal of Molecular and Cellular Cardiology*, 30(4):867-877, Apr. 1998.
Hyun et al., "Tentacle Type Peptides as Artificial Lectins against Sulfated Lewis X and A", *Bioorganic & Medicinal Chemistry Letters*, 18(14):4011-4014, Jul. 2008.
Jiang et al., "Acute Protection of Ischemic Heart by FGF-2: Involvement of FGF-2 Receptors and Protein Kinase C", *Am J Physiol Heart Circ Physiol*, 282(3):H1071-H1080, Mar. 2002.
Kawano et al., "Blockade of NF-κB Improves Cardiac Function and Survival after Myocardial Infarction", *Am. J Physiol Heart Circ Physiol*, 291:H1337-H1344, 2006.
Kelly et al., "In Vivo Phage Display Selection Yields Atherosclerotic Plaque Targeted Peptides for Imaging", *Molecular Imaging and Biology*, 8(4):201-207, 2006.
Kolonin et al., "Reversal of Obesity by Targeted Ablation of Adipose Tissue", *Nature Medicine*, 10:625-632, May 2004.
Li et al., "Gene Therapy with Extracellular Superoxide Dismutase Protects Conscious Rabbits Against Myocardial Infarction", *Circulation*, 103(14):1893-1898, Apr. 2001.
Li et al., "Gene Therapy with iNOS Provides Long-Term Protection Against Myocardial Infarction Without Adverse Functional Consequences", *Am J Physiol Heart Circ Physiol*, 290(2):H584-H589, Feb. 2006.
Lu et al., "Targeting of Embryonic Stem Cells by Peptide-Conjugated Quantum Dots", *PloS ONE*, 5(8):e12075, Aug. 2010.
McGuire et al., "In vitro Selection of a Peptide with High Selectivity for Cardiomyocytes In vivo", *Journal of Molecular Biology*, 342(1):171-182, Sep. 2004.
Melo et al., "Gene Therapy Strategy for Long-Term Myocardial Protection Using Adeno-Associated Virus-Mediated Delivery of Heme Oxygenase Gene", *Circulation*, 105(5):602-607, Feb. 2002.
Mi et al., "Identification of a Synovial Fibroblast-Specific Protein Transduction Domain for Delivery of Apoptotic Agents to Hyperplastic Synovium", *Molecular Therapy*, 8(2):295-305, Aug. 2003.
Molenaar et al., "Uptake and Processing of Modified Bacteriophage M13 in Mice: Implications for Phage Display", *Virology*, 293(1):182-191, Feb. 2002.

(Continued)

*Primary Examiner* — Amber D Steele
(74) *Attorney, Agent, or Firm* — Baker Botts, LLP

(57) ABSTRACT

The present invention relates to Cardiac Targeting Peptides or CTPs that are able to transduce cardiomyocytes specifically in culture and in vivo, and to methods for using such peptides and their derivatives to deliver peptides, proteins or nucleic acids specifically to the heart. It is based, at least in part, on the discovery that the peptide APWHLSSQYSRT (SEQ ID NO:1) functioned as a cardiac-specific protein targeting peptide and was successful in delivering a number of different cargoes to cardiac muscle cells in vitro and in vivo.

Figure 1:
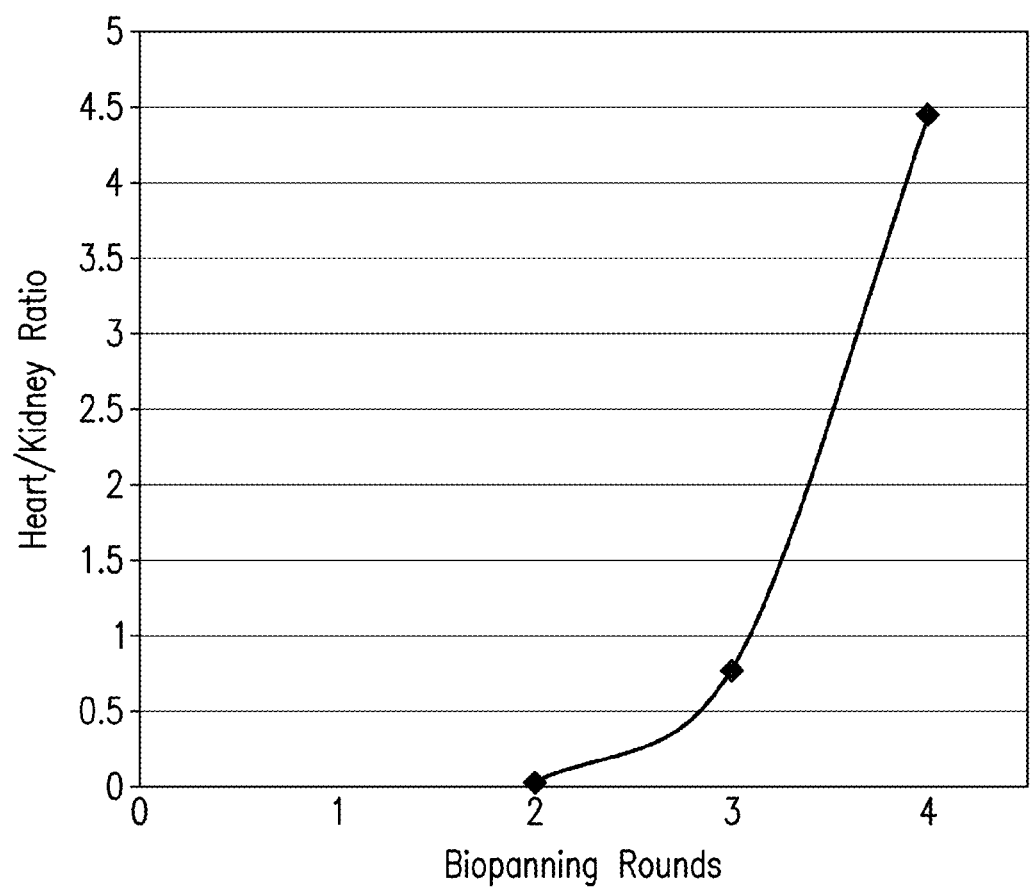

19 Claims, 23 Drawing Sheets
(12 of 23 Drawing Sheet(s) Filed in Color)

(56) References Cited

OTHER PUBLICATIONS

Okada et al., "Postinfarction Gene Therapy Against Transforming Growth Factor-β signal Modulates Infarct Tissue Dynamics and Attenuates Left Ventricular Remodeling and Heart Failure", *Circulation*, 111(19):2430-2437, May 2005.

Pachori et al., "Hypoxia-Regulated Therapeutic Gene as a Preemptive Treatment Strategy Against Ischemia/Reperfusion Tissue Injury", *PNAS*, 101(33):12282-12287, Aug. 2004.

Pasqualini et al., "Organ Targeting In Vivo Using Phage Display Peptide Libraries", *Nature*, 380(6572):364-366, Mar. 1996.

Pleger et al., "S100A1 Gene Therapy Preserves in Vivo Cardiac Function after Myocardial Infarction", *Molecular Therapy*, 12(6):1120-1129, Dec. 2005.

Rákos et al., "Evans Blue Fluorescence Permits the Rapid Visualization of Non-Intact Cells in the Perilesional Rim of Cold-Injured Rat Brain", *Acta Neurobiologiae Experimentals (Wars.)*, 67(2):149-154, 2007.

Rogers et al., "Temporal Trends in the Treatment of Over 1.5 Million Patients With Myocardial Infarction in the U.S. from 19990 Through 1999: The National Registry of Myocardial Infarction 1, 2 and 3", *Journal of the American College of Cardiology*, 36(7):2056-2063, Dec. 2000.

Roncalli et al., "Sonic Hedgehog-Induced Functional Recovery After Myocardial Infarction is Enhanced by AMD3100-Mediated Progenitor-Cell Mobilization", *Journal of the American College of Cardiology*, 57(24):2444-2452, Jun. 2011.

Segvich et al., "Identification of Peptides with Targeted Adhesion to Bone-Like Mineral via Phage Display and Computational Modeling", *Cells Tissue Organs*, 189(1-4):245-251, 2009.

Segvich et al., "The Absorption of Preferential Binding Peptides to Apatite-Based Materials", *Biomaterials*, 30(7):1287-1298, Mar. 2009.

Wakatsuki et al., "A Novel IKK Inhibitor Suppresses Heart Failure and Chronic Remodeling after Myocardial Ischemia via MMP Alteration", *Expert Opinion on Therapeutic Targets*, 12(12):1469-1476, Dec. 2008.

Whitten et al., 31st Annual Meeting Abstracts, *Western Thoracic Surgical Association*, Jun. 22-25, (Abstract) (2005) from http://www.westernthoracic.org/Abstracts/2005/10099.cgi (downloaded on Jan. 9, 2013).

Wiviott et al., "Performance of the Thrombolysis in Myocardial Infarction Risk Index in the National Registry of Myocardial Infarction-3 and -4: A Simple Index That Predicts Mortality in ST-Segment Elevation Myocardial Infarction", *Journal of the American College of Cardiology*, 44(4):783-789, Aug. 2004.

Yao et al., "Targeting Pancreatic Islets with Phage Display Assisted by Laser Pressure Catapult Microdissection", *American Journal of Pathology*, 166(2):625-636, Feb. 2005.

Zhang et al., "Molecular Profiling of Heart Endothelial Cells", *Circulation*, 112(11):601-611, Sep. 2005.

\* cited by examiner

FIGURE 2A-B
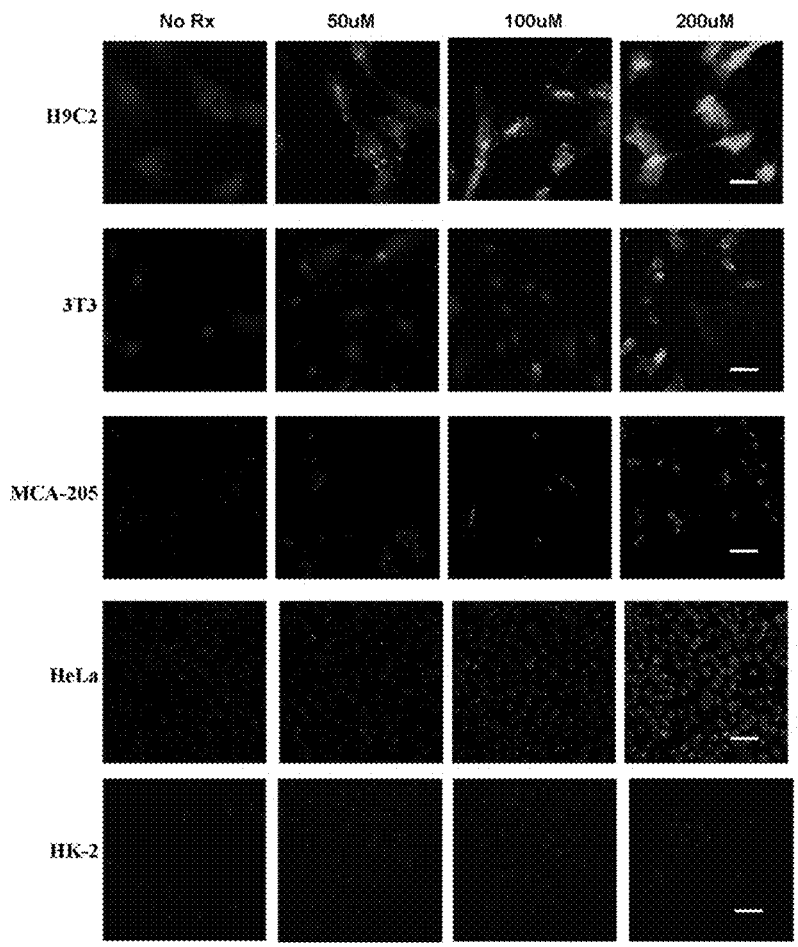
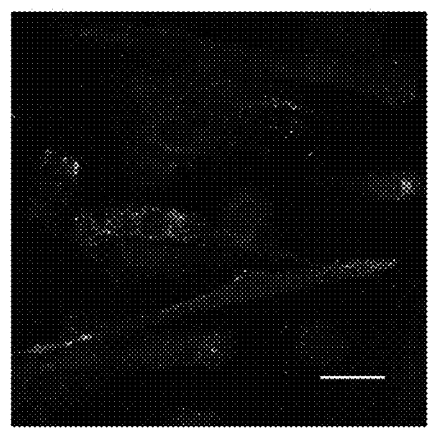

FIGURE 4A-E
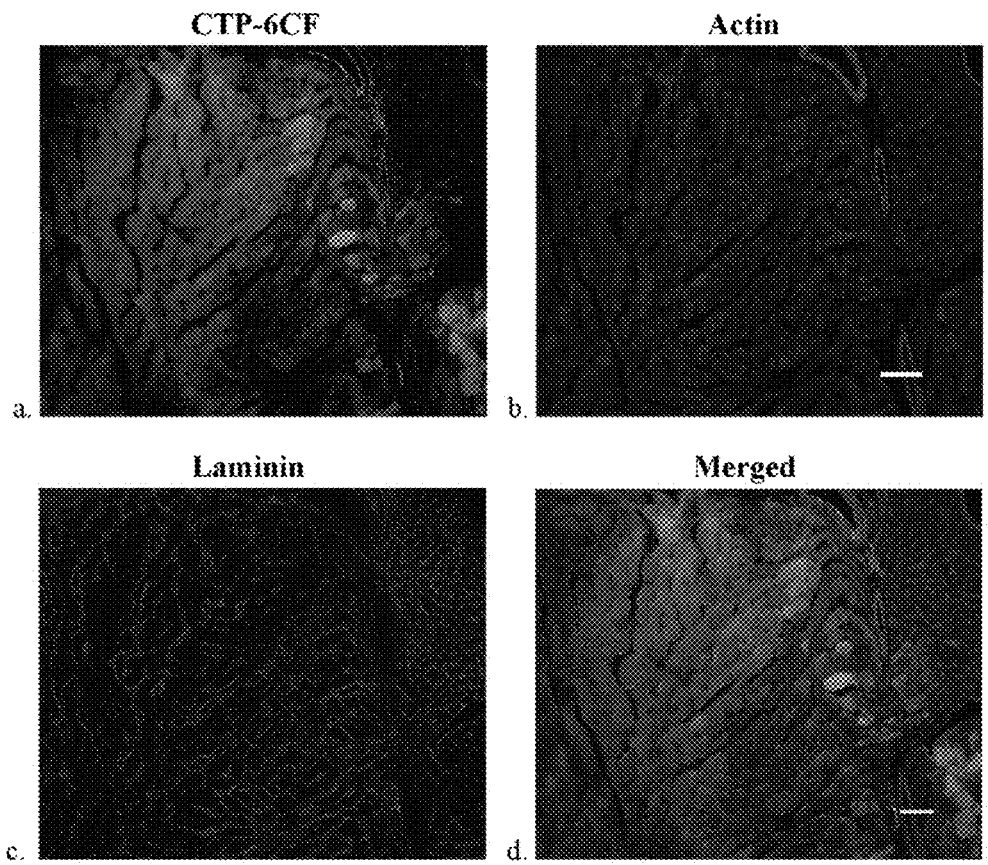
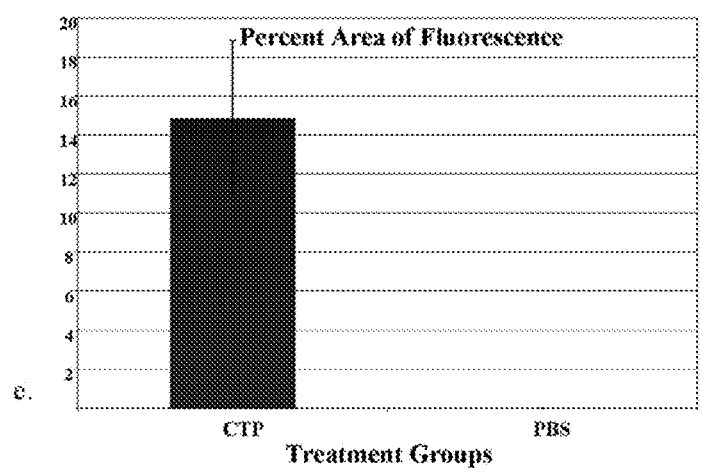

FIGURE 17
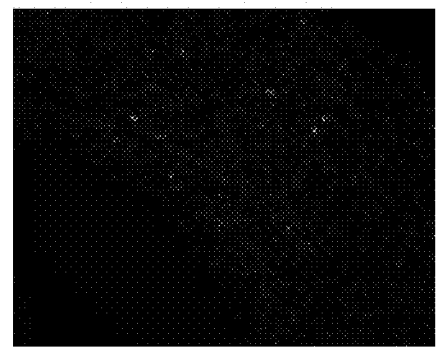
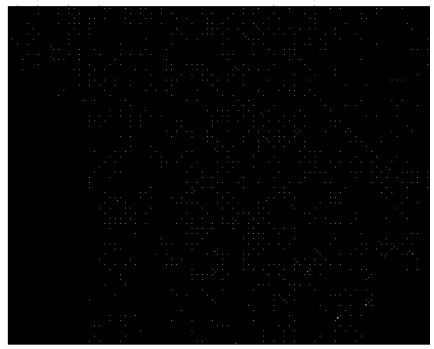

CARDIAC-SPECIFIC PROTEIN TARGETING DOMAIN

PRIORITY CLAIM

This application claims priority to U.S. Provisional Application No. 61/393,278, filed Oct. 14, 2010, the contents of which is hereby incorporated by reference in its entirety herein.

SEQUENCE LISTING

The instant application contains a Sequence Listing which has been submitted in ASCII format via EFS-Web and is hereby incorporated by reference in its entirety. Said ASCII copy, created on Jun. 4, 2012, is named 07239604.txt and is 4,902 bytes in size.

GRANT INFORMATION

This invention was made with government support under grants DAMD17-03-1-0488 and DAMD17-03-1-0142 awarded by the Department of Defense. The government has certain rights in the invention.

COLOR DRAWINGS

The patent or application file contains at least one drawing executed in color. Copies of this patent or patent application with color drawings will be provided by the Office upon request and payment of the necessary fee.

1. INTRODUCTION

The present invention relates to Cardiac-Targeting Peptides and their use in delivering molecular cargoes specifically to cells of the heart.

2. BACKGROUND OF THE INVENTION

Ischemic heart disease and occlusive coronary artery disease continue to be the number one killer in the developed world. There are an estimated 500,000 acute ST-elevation myocardial infarctions (MI) in the US alone each year [1], and this is becoming an increasingly significant problem in the developing world [2]. Current approaches for management of an acutely occluded coronary artery leading to an MI consist of anti-platelet and anti-thrombotic strategies with intervention aimed at opening the infarct-related artery in a timely fashion. Although this approach is able to protect cardiomyocytes from necrosis, with resulting decrease in morbidity and mortality, it necessitates exposing the heart to post-ischemic reperfusion injury. Limiting this reperfusion injury and decreasing apoptosis would ultimately lead to greater myocardial salvage and prevention of development of heart failure. Numerous animal studies have identified biological agents able to ameliorate this ischemia-reperfusion injury and reduce the ultimate infarct size [3, 4]. However, further development of these approaches is hindered by the inability to deliver the biologic agents to the myocardium in a tissue-specific, efficient and rapid manner. A protein transduction peptide specific for the heart would be able to deliver biologic agents in a timely fashion to the heart when given at the time of reperfusion for an infarction:

Protein transduction domains (PTD) are small cationic peptides that can cross cellular membranes, and are able to transport large, biologically active molecules into mammalian cells in culture as well as in vivo. The limitation of PTDs is the non-specific transduction of all tissue types with some tissues, such as liver and kidney, taking up the PTD much more avidly than heart tissue. Thus there is a need to identify peptides able to target cardiac tissue specifically for delivery of biologics of therapeutic potential.

Screening approaches using peptide phage display libraries are effective for identifying peptides able to bind to specific ligand targets as well as identifying peptides with novel properties. Phage display uses filamentous bacteriophage, such as M13, that are able to replicate in *E. coli*. The proteins or peptides to be displayed are fused to the N-terminus of phage coat protein pIII or pVIII and thus are present on the surface of the phage. Screening of peptide phage display libraries has been used in vivo to identify peptides able to target tumor vasculature [5], adipose tissue [6] and pancreatic islet cells [7]. In addition, it has been used to identify peptides able to facilitate internalization of intact, infectious phage into specific cell types such as synovial fibroblasts [8]. In vivo phage display also has been utilized to target atherosclerotic plaques [9], and to probe the heart vasculature for endothelial markers [10]. Although in vitro selection of a specific peptide sequence carrying phage resulted in increased targeting of cardiomyocytes by phage in vivo [11], it remains to be determined if the peptide can actually deliver "cargo" peptides or proteins of therapeutic potential to the heart. If such were indeed the case, it would open up new avenues of drug development, leading to delivery of therapeutics directly to the ischemic heart.

3. SUMMARY OF THE INVENTION

The present invention relates to Cardiac Targeting Peptides or CTPs that are able to transduce cardiomyocytes specifically in culture and in vivo, and to methods for using such peptides and their derivatives to deliver peptides, proteins or nucleic acids specifically to the heart. It is based, at least in part, on the discovery that the peptide APWHLSSQYSRT (SEQ ID NO:1) functioned as a cardiac-specific protein transduction peptide and was successful in delivering a number of different cargoes to cardiac muscle cells in vitro and in vivo.

4. BRIEF DESCRIPTION OF THE FIGURES

FIG. 1. Enrichment of cardiac specific phage by multiple rounds of biopanning. After a single, screening cycle of phage incubated with H9C2 cells, recovered phage was amplified, titered and injected intravenously into Balb/c mice. After a circulation time of 24 hours, mice were euthanized, heart and kidney dissected, digested with collagenase II, cells lysed and recovered phage tittered. Recovered phage was amplified, re-titered and injected for subsequent round of biopanning. Phage recovered from heart versus kidney from each cycle of in vivo phage display was normalized by gram of tissue weight and expressed as a ratio of heart to kidney.

FIG. 2A-B. CTP specifically transduces cardiomyocytes in culture. Confocal micrographs of H9C2, 3T3, MCA-205, HeLa and HK-2 cells incubated with increasing concentrations (50 uM, 100 uM and 200 uM) of CTP-6CF for 30 minutes, followed by multiple washings and cross-staining with a nuclear stain, DRAQ5 (206) (A). A higher (406) confocal micrograph of H9C2 cells is shown demonstrating pattern of transduction (B); CTP-6CF—green, Nuclei—blue. Scale bars represent 100 uM.

Figure 3A:
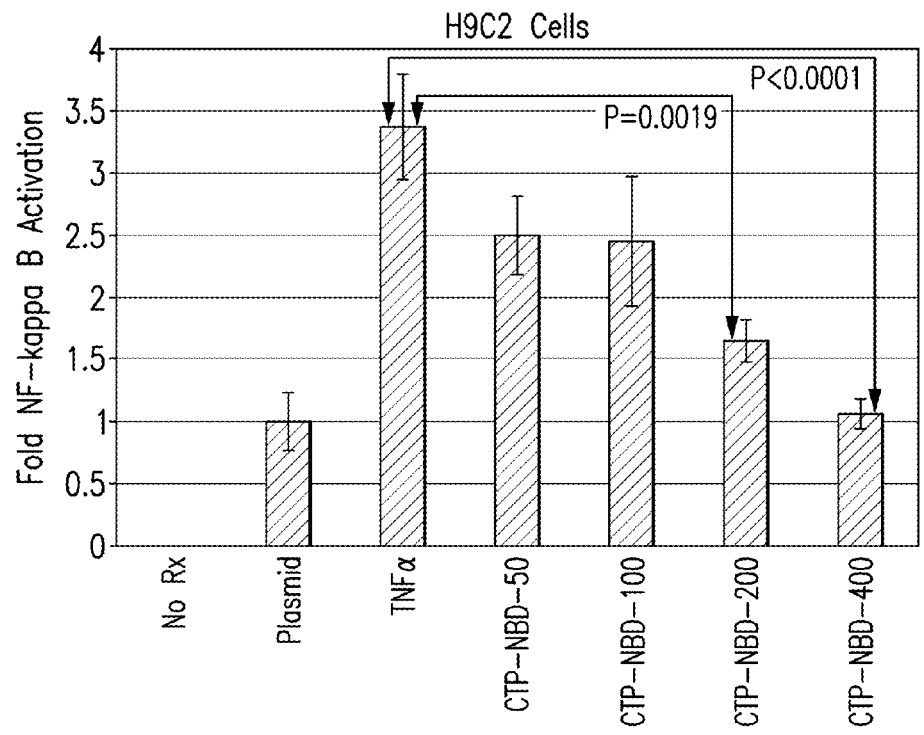
Figure 3B:
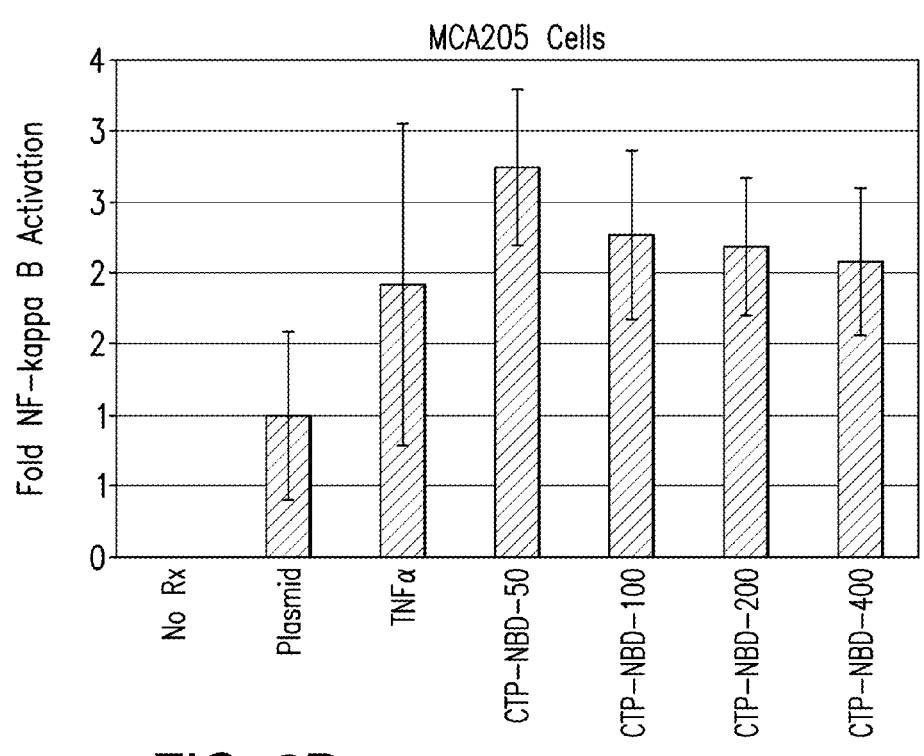

FIG. 3A-B. CTP functionally delivers the IKK/NF-kB inhibitory peptide NBD to cardiomyocytes. H9C2 cells (A) and MCA205 (B) cells, were co-transfected with a NF-kB dependent luciferase reporter plasmid and a control *renilla*-expression plasmid. Twenty-four hours post-transfection, cells were stimulated with TNF-a (10 ng/ml) or pre-treated with increasing concentrations of CTP-NBD (50 uM, 100 uM, 200 uM and 400 uM) for 30 minutes followed by TNF-a stimulation for three hours. Cells were then washed, lysed and luciferase activity measured and normalized to *renilla* activity. (N=4 in each group; error bars represent one standard deviation).

FIG. 4A-E. Internalization and quantification of transduction by CTP-6CF in cardiac tissue in vivo. Cross-sections of mouse heart were stained for actin (blue) and laminin (red). Confocal microscopy showed co-localization of CTP-6CF (A) with actin (B) but not laminin (C) as seen in the color-merged micrograph (D). FITC fluorescence from non-overlapping heart micrographs from mice injected with CTP-6CF (n=3) or PBS (n=3) was quantified and expressed as a percentage of total area calculated from staining for actin (E; error bars represent standard error of the mean). CTP-6CF—green; Actin—blue; Laminin—red. Scale bars represent 100 uM.

Figure 5:
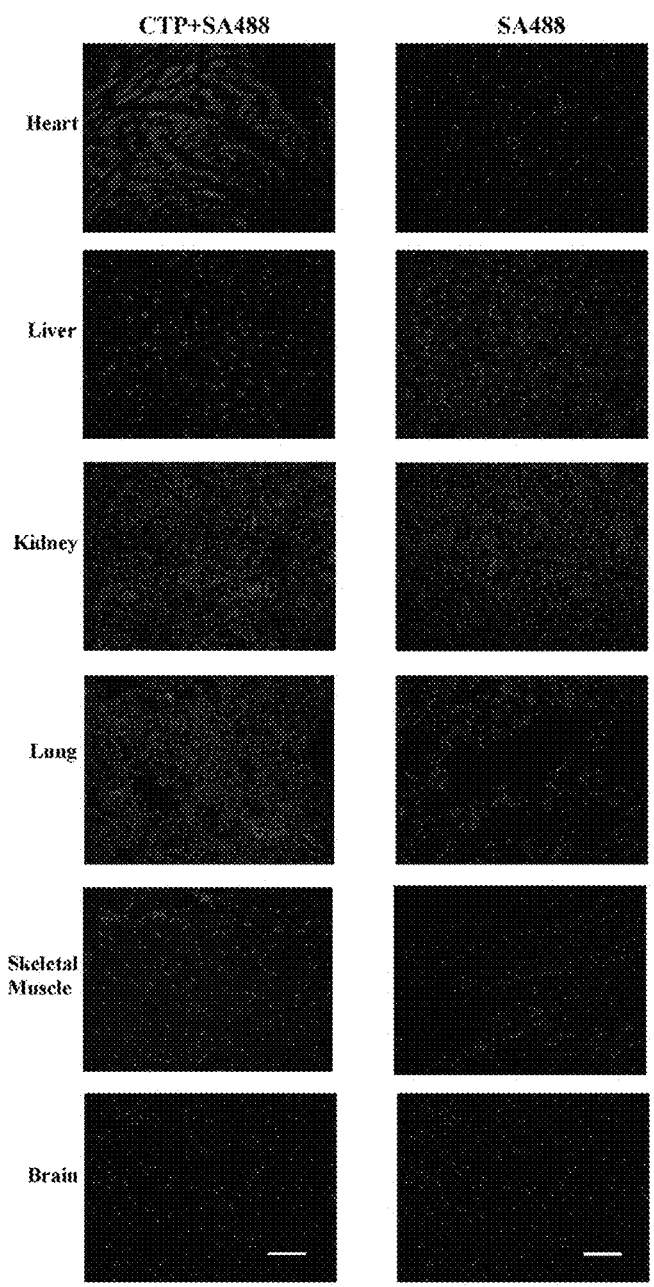

FIG. 5. CTP specifically transduces cardiac tissue in vivo. Confocal analysis (206) was performed on tissues from heart, liver, kidney, lung, skeletal muscle and brain from mice euthanized 30 minutes after intravenous injection of CTP-biotin-SA488 conjugate (10 mg/Kg) or PBS+SA488. Slides were counter-stained with DRAQ5, a nuclear stain. CTP-SA488—green, Nuclei—blue. N=3 in each group; scale bars represent 100 uM.

Figure 6:
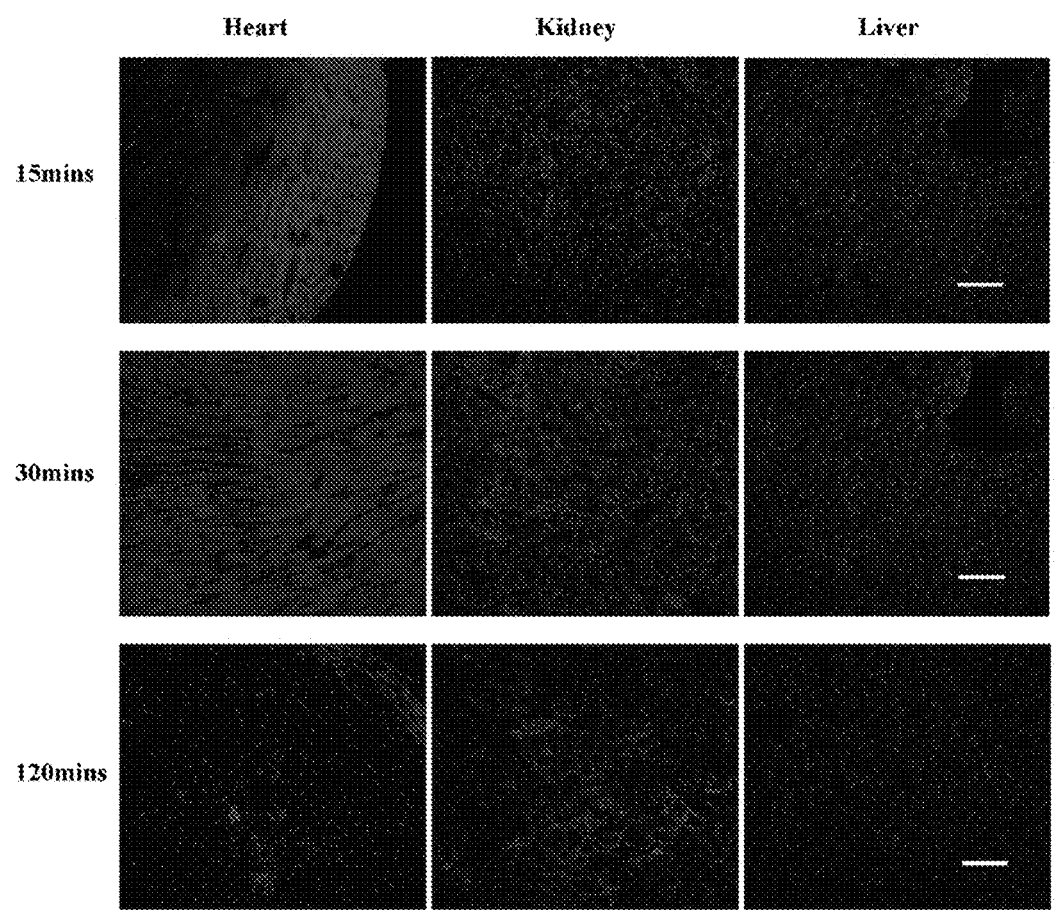

FIG. 6. Pattern of distribution of CTP-biotin-SA488 over time in vivo. Mice were injected intravenously with CTP-biotin-SA488 (10 mg/Kg) and euthanized 15, 30 or 120 minutes post-injection. Heart, kidneys and liver were cross-sectioned, counter-stained with DRAQ5 and confocal microscopy performed. N=1 in each group; scale bars represent 100 uM.

Figure 7:
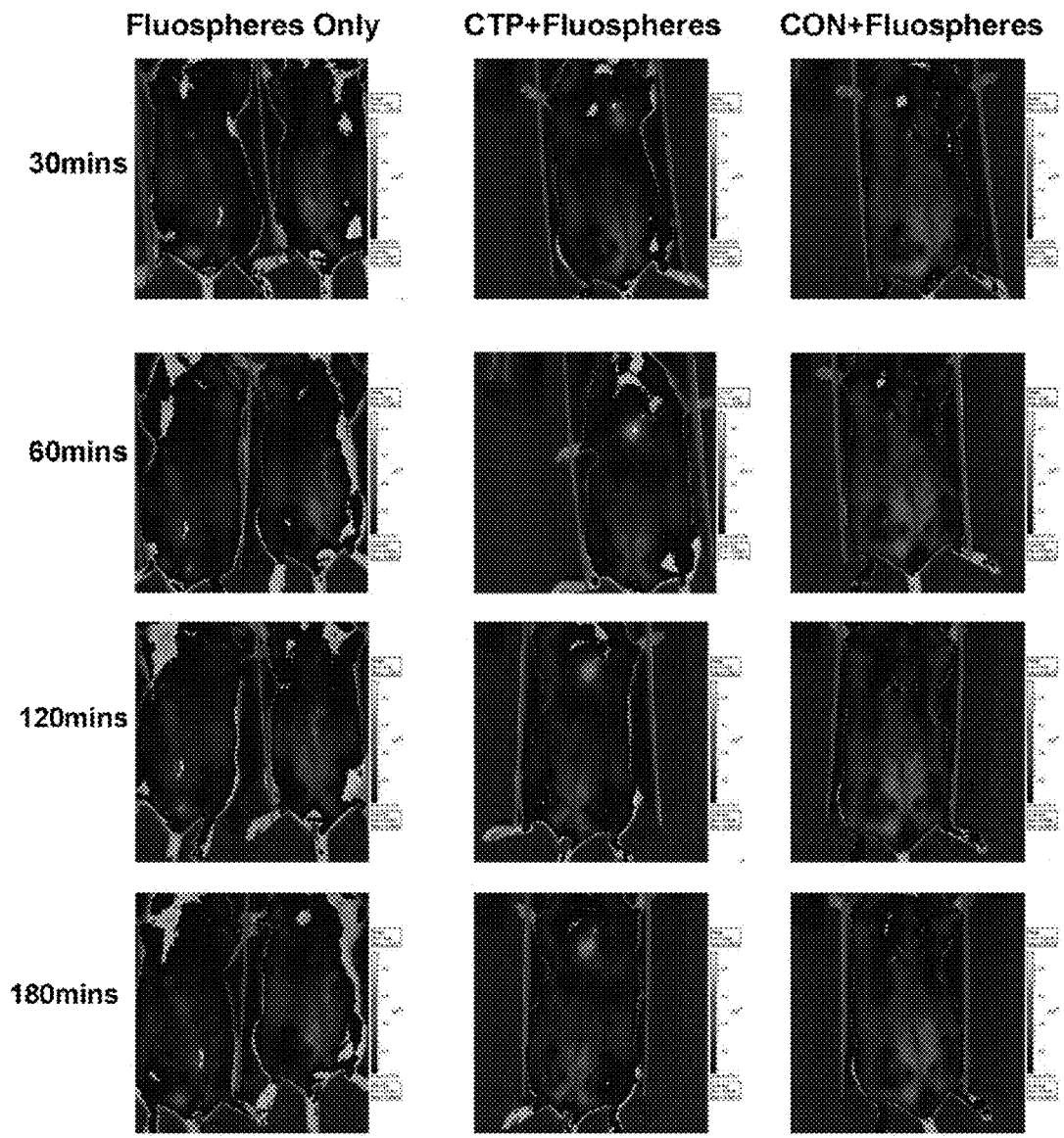

FIG. 7. CTP targets fluospheres to the heart. Whole mouse in vivo imaging was performed following intra-cardiac injection of fluospheres alone, CTP+fluospheres and RAN+fluospheres at 30, 60, 120 and 180 minutes, at a dose of 10 mg/Kg of body weight (for peptides). (N=3 in each group).

Figure 8:
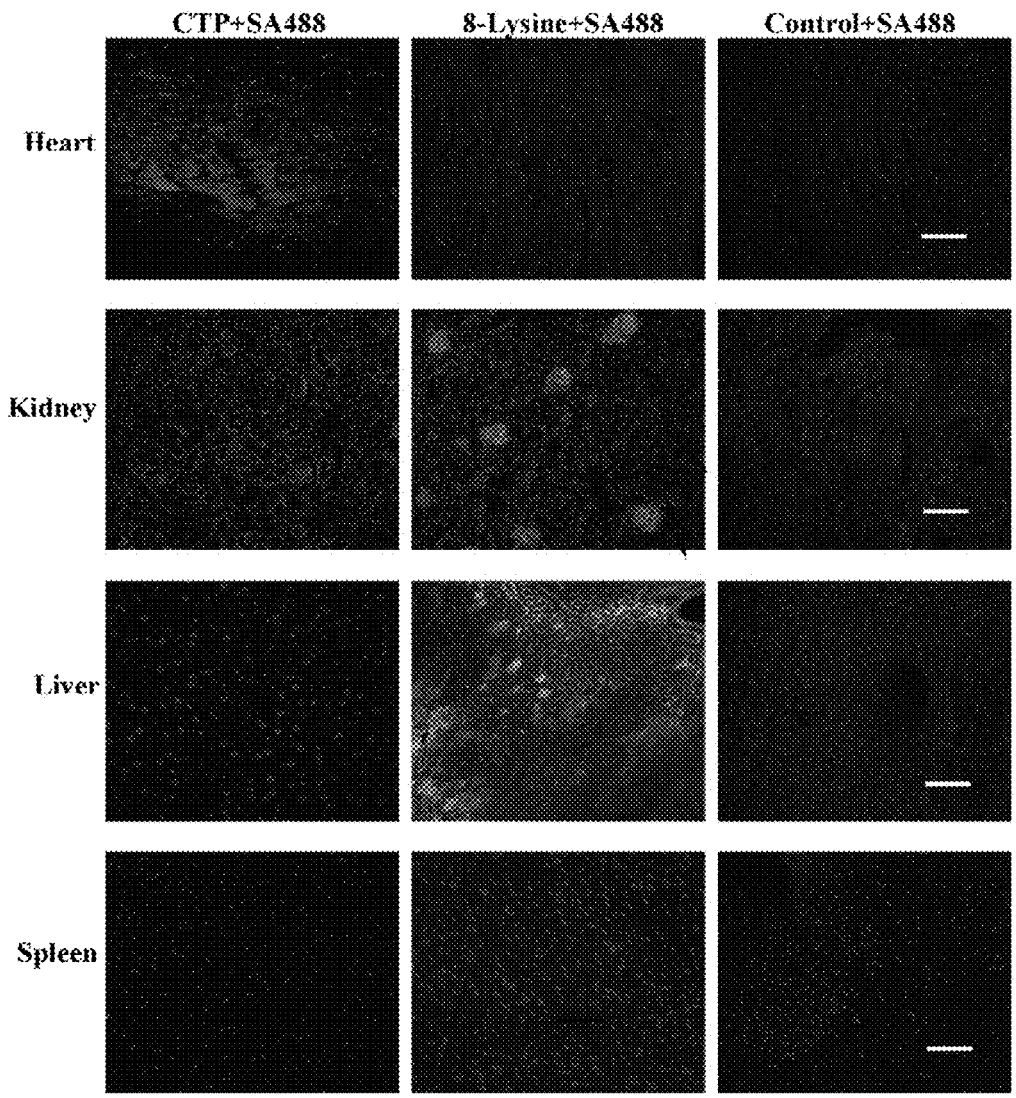

FIG. 8. CTP specifically transduces cardiac tissue in contrast to a cationic transduction domain. Confocal analysis of heart, kidney, liver and spleen 30 minutes following intravenous injection of CTP+SA488, 8K+SA488 or RAN+SA488 (10 mg/Kg body weight) conjugates. N=2 in each group; scale bars represent 100 uM.

Figure 9:
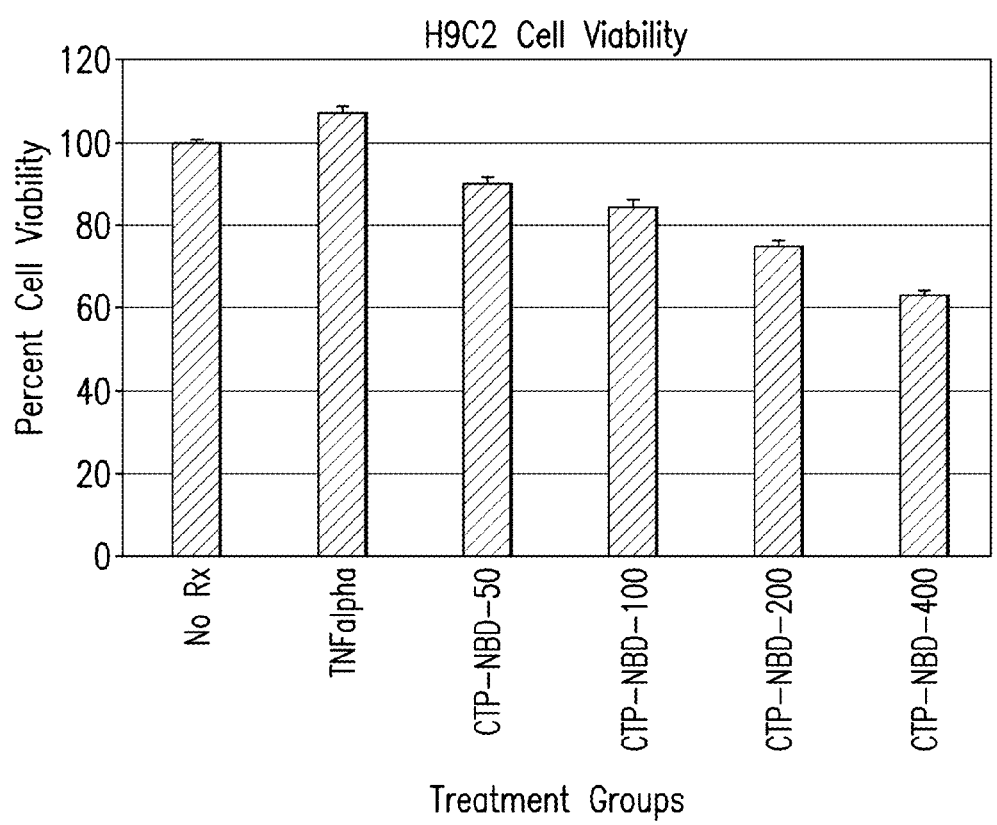

FIG. 9. H9C2 cell viability after transfection, treatment with CTP-NBD and subsequent TNF-alpha treatment.

Figure 10:
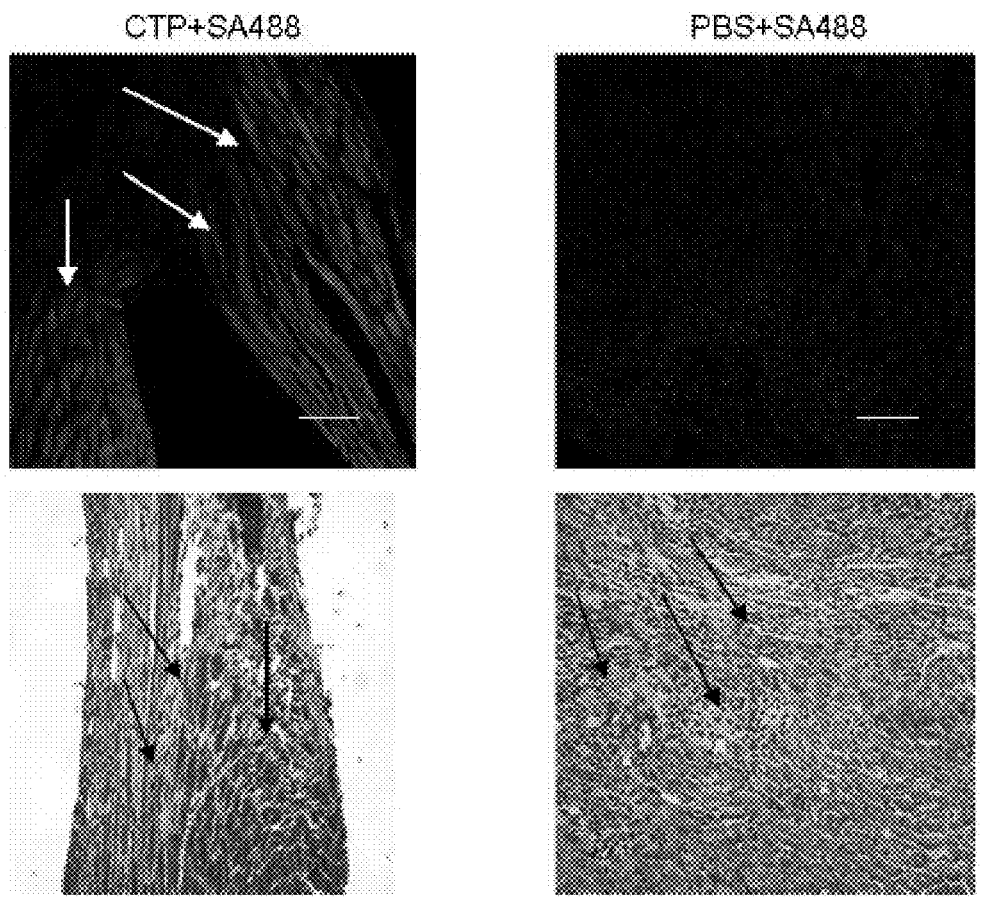

FIG. 10. Uptake of CTP-6CF preferentially by normal myocardium with exclusion from the infarct area.

Figure 11:
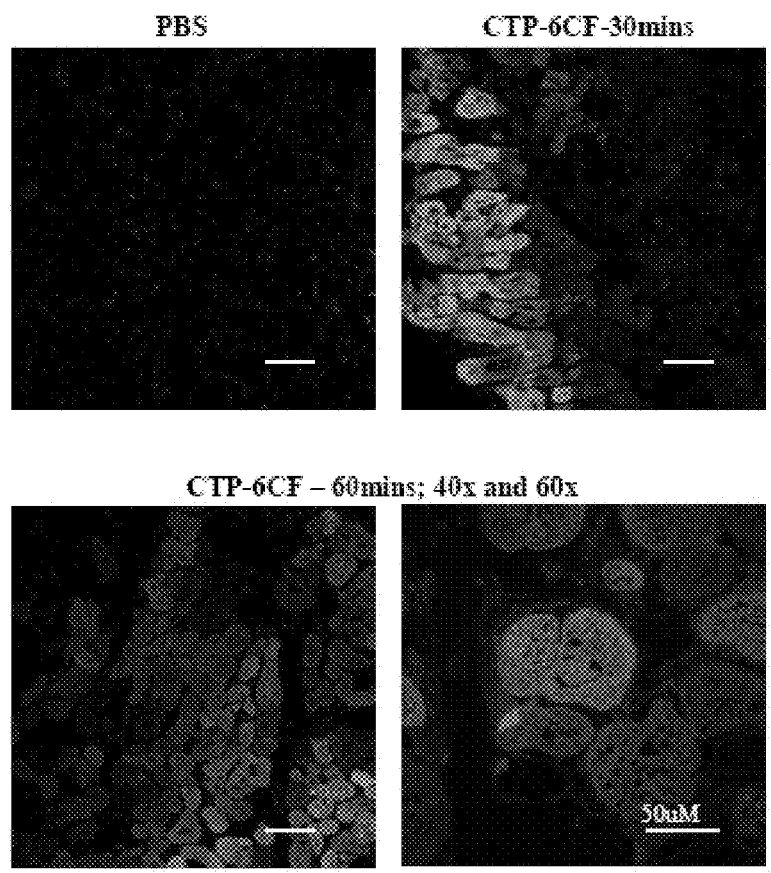

FIG. 11. Transduction of human heart tissue ex vivo by CTP-6CF.

Figure 12:
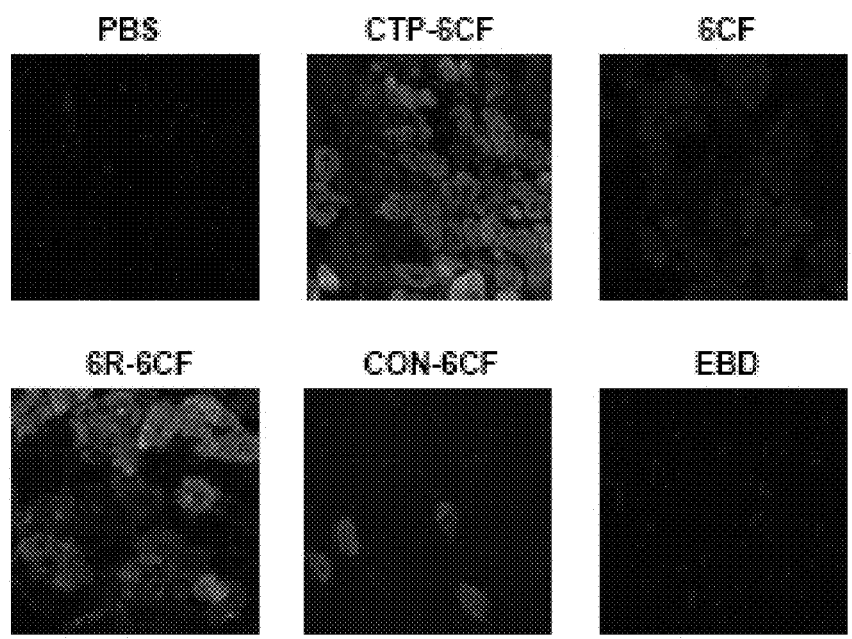

FIG. 12. Results of ex vivo human heart tissue experiment at 30 mins.

Figure 13:
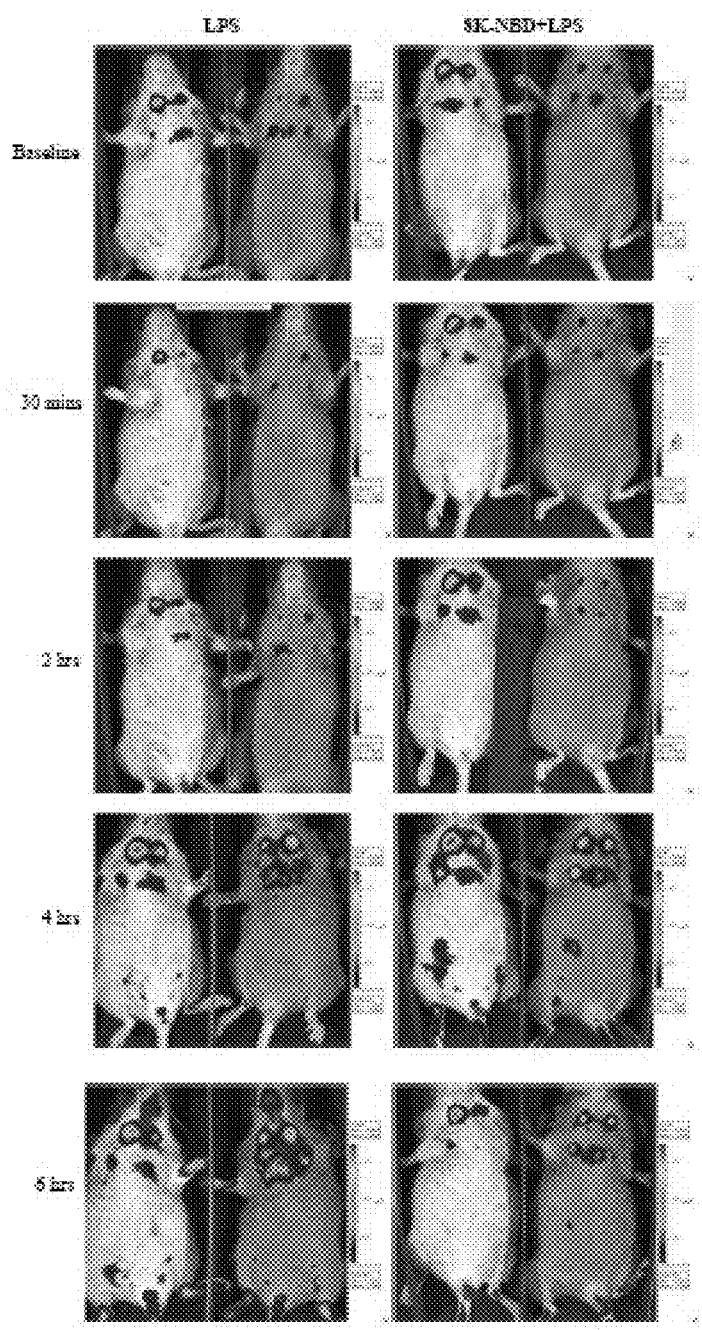

FIG. 13. Inhibition of LPS induced Luciferase signal by 8K-NBD.

Figure 14:
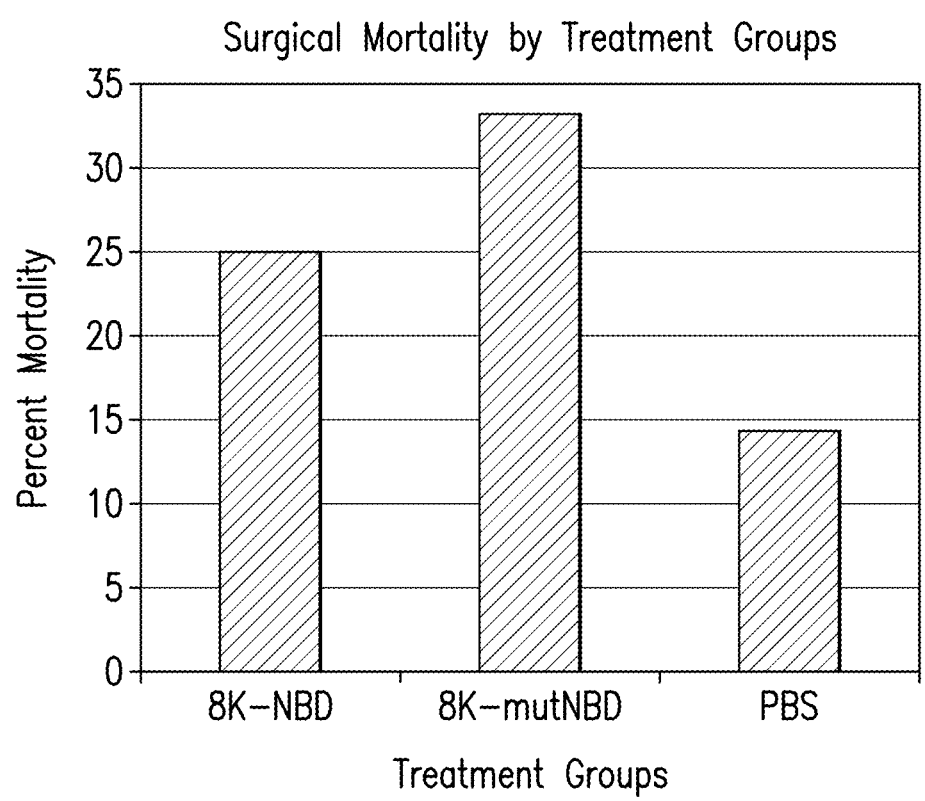

FIG. 14. Post-operative mortality by treatment group in the 8K-NBD study.

Figure 15:
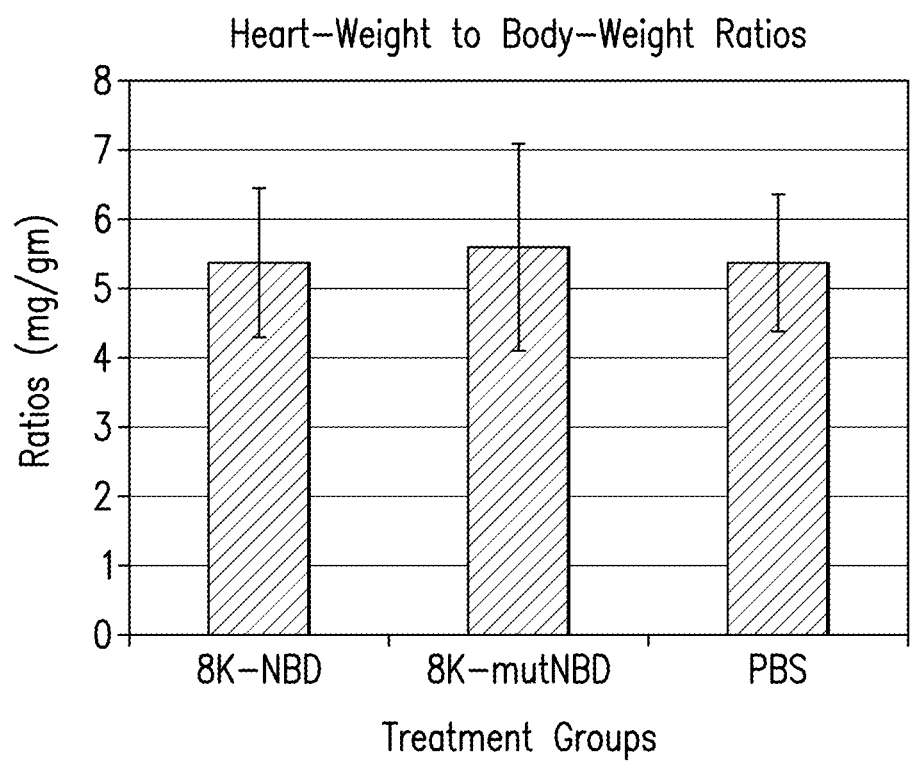

FIG. 15. Heart weight to body weight ratios across the treatment groups in the 8K-NBD study.

Figure 16:
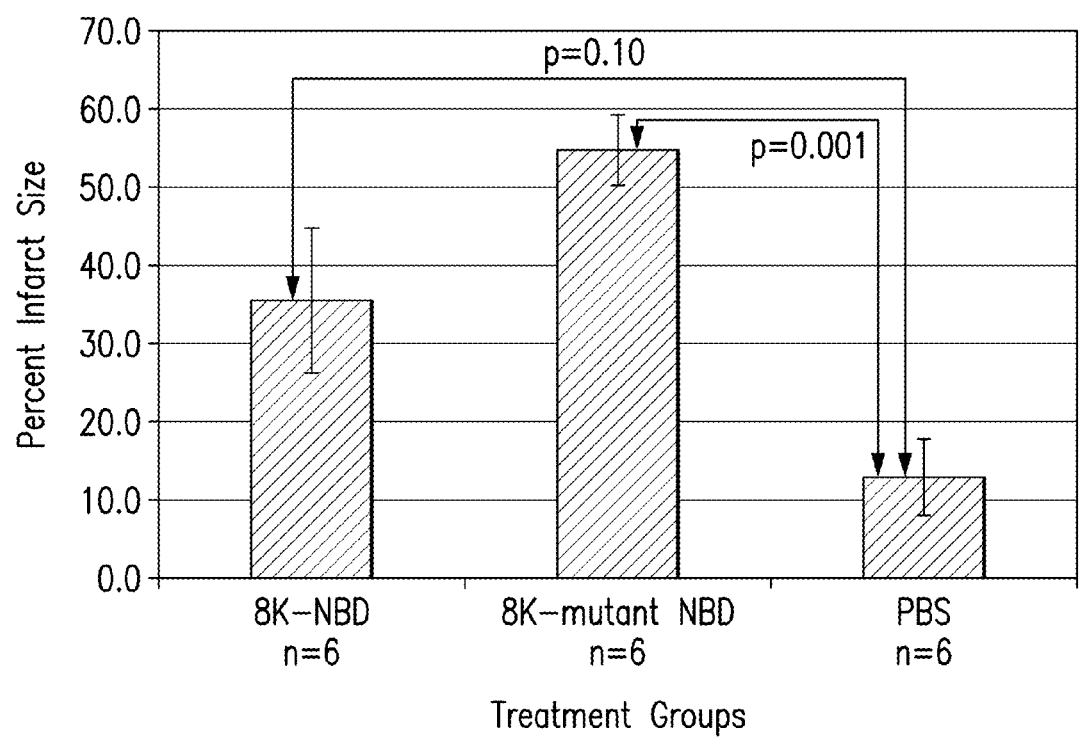

FIG. 16. Infarct size across different treatment groups in the 8K-NBD study.

FIG. 17. Representative confocal micrographs of TUNEL staining in each treatment group in the 8K-NBD study.

Figure 18:
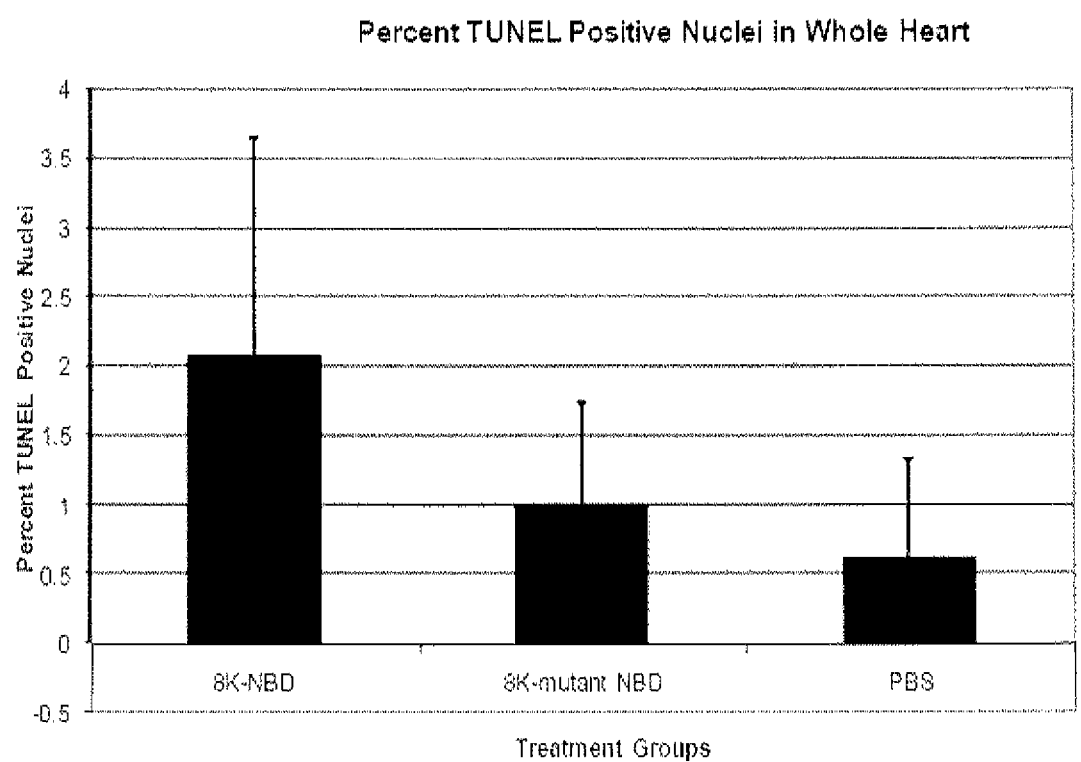

FIG. 18. Quantification of TUNEL positive data in each treatment group in 8K-NBD study.

Figure 19:
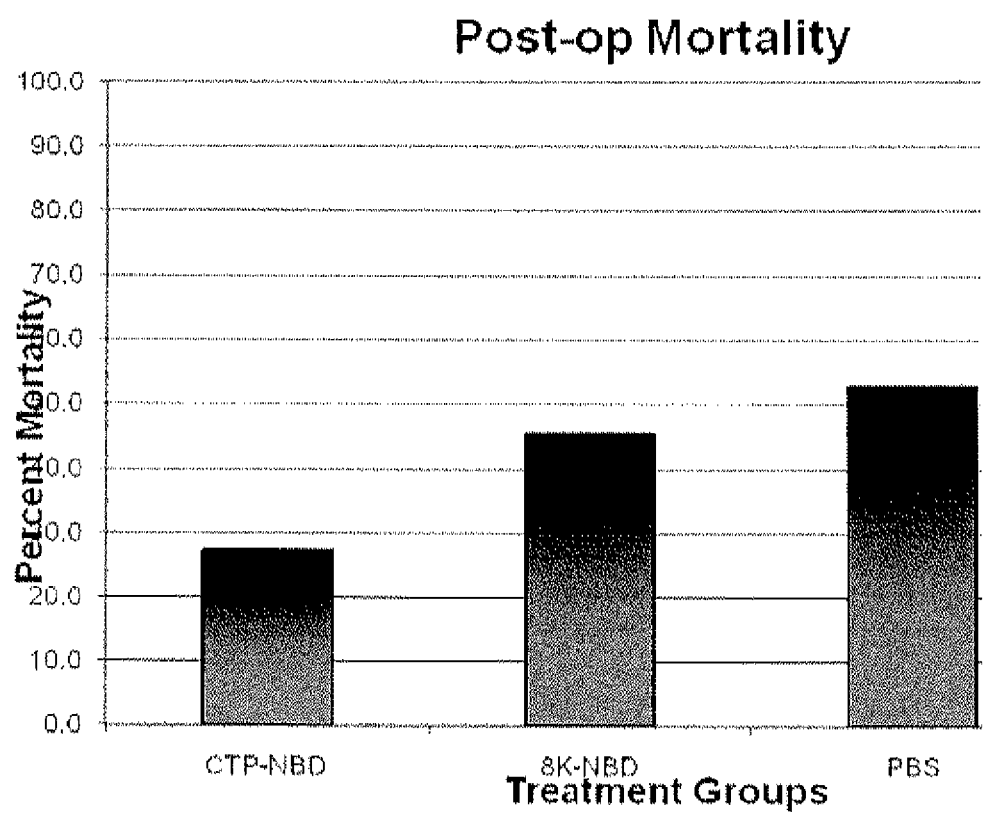

FIG. 19. Post-operative mortality by treatment group in the CTP-NBD study.

Figure 20:
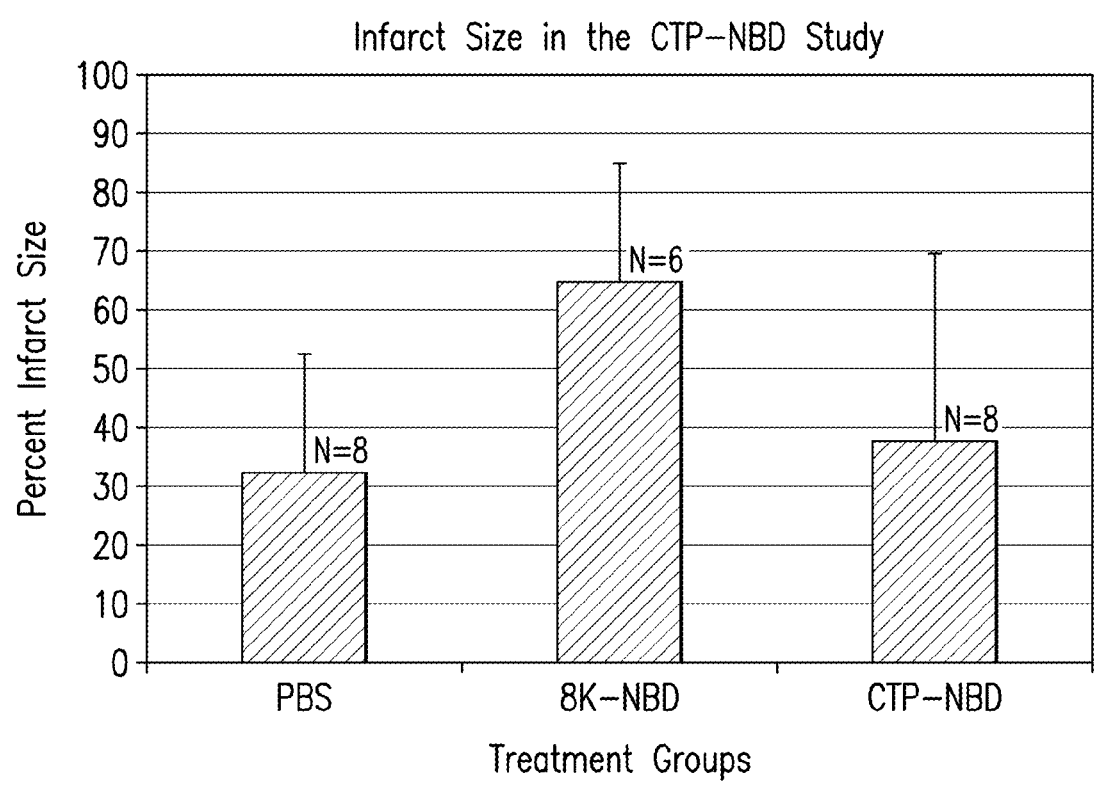

FIG. 20. Infarct size by treatment groups in the CTP-NBD study.

Figure 21:
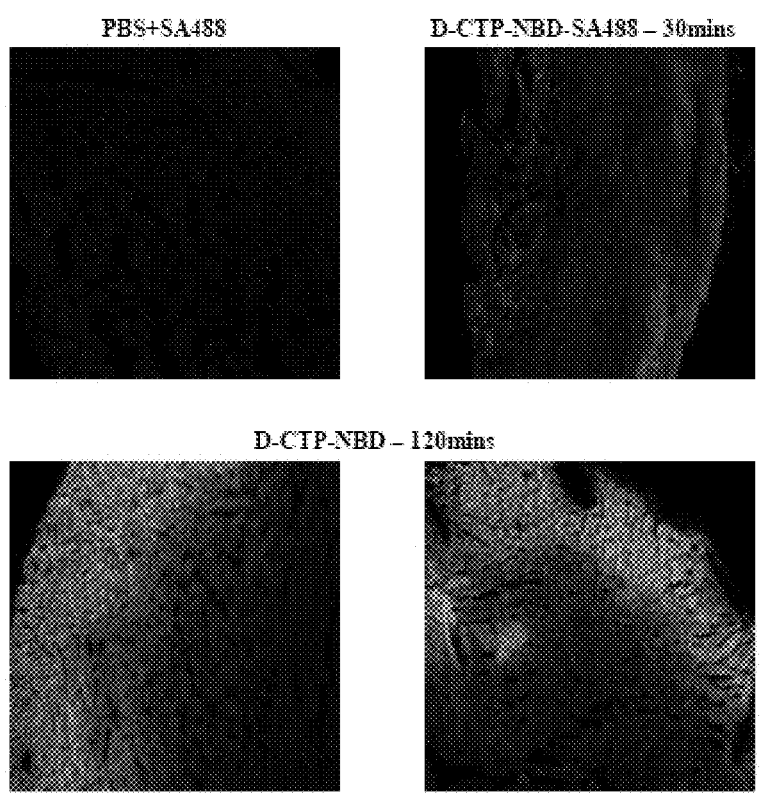

FIG. 21. Transduction of the mouse heart by the D-CTP-NBD-SA488 complex.

Figure 22:
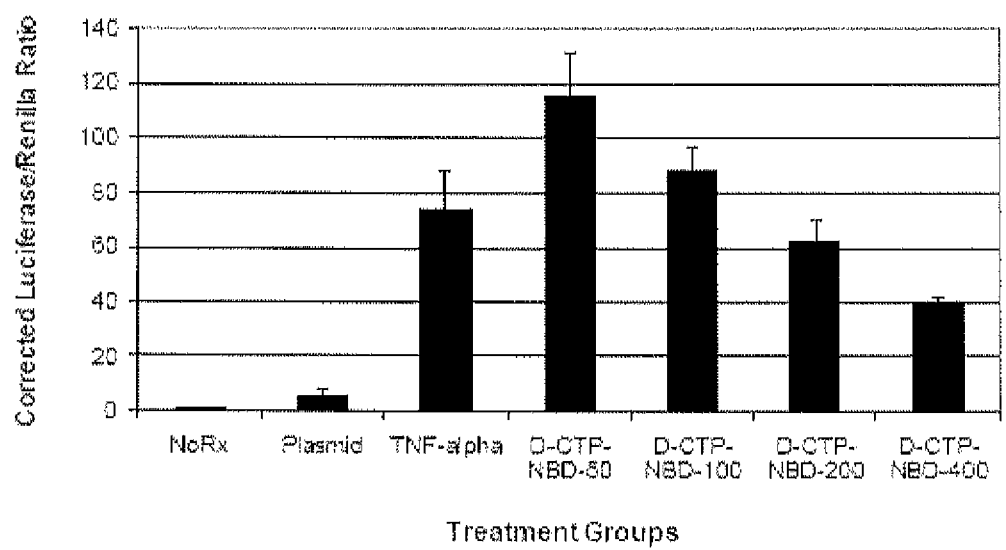

FIG. 22. Inhibition of NF-κB activation by the D-isoform of CTP-NBD.

Figure 23:
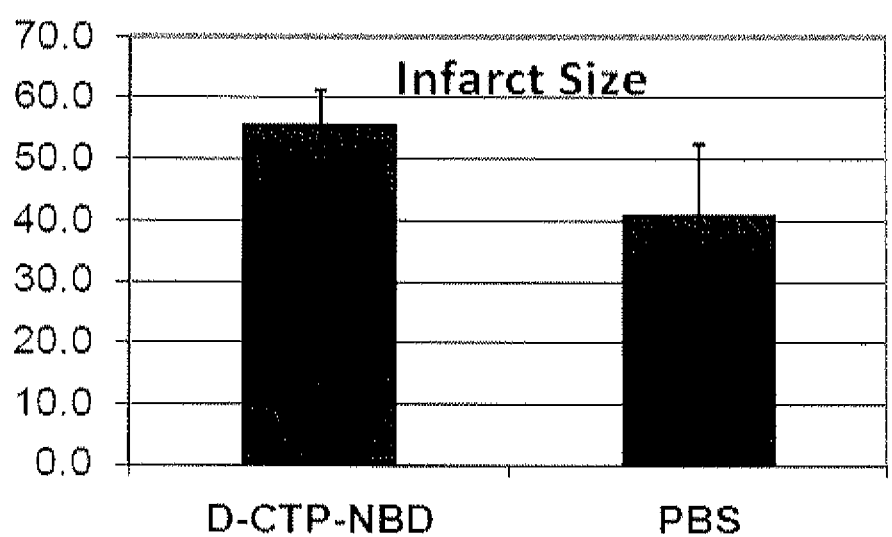

FIG. 23. Infarct sizes in the two treatment groups.

5. DETAILED DESCRIPTION OF THE INVENTION

For purposes of clarity and not by way of limitation, the detailed description of the invention is divided into the following subsections:
(i) cardiac targeting peptides;
(ii) cargo;
(iii) linkers;
(iv) methods of use.

5.1 Cardiac Targeting Peptides

The present invention provides for Cardiac Targeting Peptides ("CTP"). In certain non-limiting embodiments the CTP specifically targets cardiac tissue. "Specifically targets cardiac tissue" means that when said CTP, linked to a cargo molecule to form a CTP-cargo complex, is injected into a mammal, the CTP-cargo complex is transduced into cardiac tissue at much higher levels than it is transduced into other tissues, such as, for example, liver, kidney, lung, skeletal muscle, or brain. In certain embodiments the ratio of transduction of a CTP that "specifically targets cardiac tissue" into cardiac tissue relative to liver, kidney, lung, skeletal muscle or brain is at least 2:1 or is at least 3:1.

In certain non-limiting embodiments, the CTP has the amino acid sequence APWHLSSQYSRT (SEQ ID NO:1).

In certain non-limiting embodiments, the CTP has an amino acid sequence which is APWHLSSQYSRT (SEQ ID NO:1) or a variation thereof in which one amino acid is either deleted, substituted by another amino acid, or one amino acid is added.

In certain non-limiting embodiments, the CTP has an amino acid sequence which is APWHLSSQYSRT (SEQ ID NO:1) or a variation thereof in which one or two amino acids is/are either deleted, substituted by another amino acid, or one or two amino acid is added.

In certain non-limiting embodiments, the CTP is a peptide that is between 8 and 12 amino acids in length or between 8 and 10 amino acids in length that comprises the sequence HLSSQYSR (SEQ ID NO:2) or a variation thereof in which one amino acid is either deleted, substituted by another amino acid, or one amino acid is added.

Non-limiting examples of CTPs of the invention include:

```
                                              (SEQ ID NO: 3)
APWHLSSQYSR;

(SEQ ID NO: 4)
PWHLSSQYSRT;

(SEQ ID NO: 5)
PWHLSSQYSR;

(SEQ ID NO: 6)
APX₁HLSSQYSRT
where X₁ is W or Y;
```

-continued

```
                                                    (SEQ ID NO: 7)
APWHLSSQ X₁SRT
where X₁ is W or Y;

(SEQ ID NO: 8)
PX₁HLSSQYSRT
where X₁ is W or Y;

(SEQ ID NO: 9)
PWHLSSQ X₁SRT
where X₁ is W or Y;

(SEQ ID NO: 10)
X₁HLSSQYSRT
where X₁ is W or Y;

(SEQ ID NO: 11)
WHLSSQ X₁SRT
where X₁ is W or Y;

(SEQ ID NO: 12)
X₁HLSSQYSR
where X₁ is W or Y;

(SEQ ID NO: 13)
WHLSSQ X₁SR
where X₁ is W or Y;
```

In certain non-limiting embodiments the CTP has a net charge of between about +0.8 to +1.2 at pH=7. In certain non-limiting embodiments the CTP has a net charge of about 1.1 at pH=7.

In certain non-limiting embodiments, the CTP has an isoelectric point at between pH 9 and pH 9.5. In certain non-limiting embodiments, the CTP has an isoelectric point at pH 9.35.

In certain non-limiting embodiments, the CTP has an average hydrophilicity index of between −0.2 and −0.6. In certain non-limiting embodiments, the CTP has an average hydrophilicity index of −0.4.

In certain non-limiting embodiments, the CTP is comprised of (L) amino acids.

In certain non-limiting embodiments, the CTP is comprised of (D) amino acids.

5.2 Cargo

According to the invention, the CTP is linked with a cargo molecule to form a complex, optionally via a linker molecule or molecules.

The cargo molecule may be a protein (including a glycoprotein), a nucleic acid, a carbohydrate, a lipid, or a combination thereof.

In certain non-limiting embodiments, the cargo is a protein. In certain non-limiting embodiments, the protein is selected from the group consisting of a cytokine, a growth factor, an enzyme, an ion channel, and an anti-inflammatory protein.

In certain non-limiting embodiments, the cargo is an antioxidant.

In certain non-limiting embodiments, the cargo is a nucleic acid. Non-limiting examples of such nucleic acid include DNA, RNA, antisense RNA, interfering RNA, microRNA, catalytic RNA, and catalytic DNA.

One specific non-limiting example of a cargo is a NF-κB inhibitor, for example NBD peptide TALDWSWLQTE (SEQ ID NO:14).

One specific non-limiting example of a cargo is heme oxygenase, for example human heme oxygenase (23).

One specific non-limiting example of a cargo is inducible nitric oxide synthase ("iNOS"), for example human iNOS (24).

One specific non-limiting example of a cargo is S100A1 (an inotropic regulator of myocardial contractility; 25)

One specific non-limiting example of a cargo is extracellular superoxide dismutase (26).

Further specific non-limiting examples of cargo include Cu/Zn-SOD, Mn-SOD, catalase, and glutathione peroxidase (27).

One specific non-limiting example of a cargo is transforming growth factor beta ("TGF-β") type II receptor (Ad.CAG-sTβRII), a competitive inhibitor of TGF-β (28).

One specific non-limiting example of cargo is VEGF (vascular endothelial growth factor), for example human VEGF (29).

One specific non-limiting example of a cargo is fibroblast growth factor (FGF), for example human FGF-1 or FGF-2 (30-31).

One specific non-limiting example of a cargo is hepatocyte growth factor ("HGF").

One set of non-limiting examples of cargo is an apoptosis inhibitor, such as one of the so-called inhibitors of apoptosis ("IAPs"), for example, the human IAPs c-IAP1, c-IAP2, and XIAP.

One specific non-limiting example of a cargo is Sonic Hedgehog protein (32).

One specific non-limiting example of a cargo is glucocerebrosidase, for example human glucocerebrosidase used for treatment in Gaucher's disease.

One specific non-limiting example of cargo is a RNAi that inhibits expression of TGFβ.

In another set of non-limiting embodiments, the cargo is a nanoparticle or a microsphere containing a diagnostic or therapeutic agent.

In another set of non-limiting embodiments, the cargo is a vector comprising a therapeutic gene, for example an adenovirus vector or a lentivirus vector.

In another set of non-limiting embodiments, the cargo is a detectable compound for analysis of uptake in viable cardiac cells versus non viable cells following ischemic injury. Non-limiting examples of detectable compounds include fluorodeoxyglucose, a technetium 99 or other radioisotope-labelled cargo, fluorescent markers, gadolinium markers, etc. One non-limiting example of a radioisotope-labelled cargo is Sestamibi, a coordination complex of the radioisotope technetium-99m with the ligand methoxyisobutylisonitrile ("MIBI").

5.3 Linkers

The CTP and the cargo are linked covalently or non-covalently, optionally via one or more linker molecule.

Where the bond is a covalent bond, CTP and cargo, optionally with a linker(s) between, may be joined via one or more peptide bond, thioester bond, thioether bond, carbamate bond, etc., which can be created according to methods generally and well known in the art.

In certain non-limiting embodiments the linker is a peptide. In specific non-limiting embodiments the peptide has a length of between about 1 and 50 or between about 1 and 20 or between about 1 and 15 or between about 1 and 10 or between about 1 and 5 amino acids. In certain embodiments, the linker may comprise a cleavage site that may, upon enzymatic or chemical cleavage, release the CTP from its cargo.

In certain non-limiting embodiments, the linker may be a ligand pair. As one specific example, the linker may be an avidin/biotin pair.

Accordingly, the invention provides for a complex comprising a CTP linked to a cargo. The complex may comprise additional elements. For example, the CTP and/or cargo may be conjugated to one or more additional molecule that improves delivery or stability. As one non-limiting example, the CTP and/or cargo may be PEGylated. As another non-limiting example, the cargo may be linked to a nuclear transport peptide. As another non-limiting example, the cargo may be linked to a detectable compound.

5.4 Methods of Use

The present invention provides for a method of introducing a cargo into a cardiac tissue comprising administering, to the cardiac tissue, a complex comprising a CTP linked to the cargo molecule.

The present invention provides for a method of introducing a cargo into a cardiac muscle cell comprising administering, to the cardiac muscle cell, a complex comprising a CTP linked to the cargo.

The present invention provides for a method of selectively delivering a cargo to cardiac tissue in a subject, comprising administering, to the subject, a complex comprising a CTP linked to the cargo.

The present invention provides for a method of selectively delivering a cargo to a cardiac muscle cell in a subject, comprising administering, to the subject, a complex comprising a CTP linked to the cargo.

The present invention provides for a method of treating a subject suffering from a myocardial infarction, comprising administering, to the subject, a therapeutically effective amount of a complex comprising a CTP linked to the cargo, where the cargo (meaning the biological function of the cargo) inhibits cell death, inhibits arrhythmias, improves contractility, lengthens subject survival, or a combination thereof.

The present invention provides for a method of treating a subject suffering from angina, comprising administering, to the subject, a therapeutically effective amount of a complex comprising a CTP linked to a cargo, where the cargo reduces the risk of myocardial infarction, inhibits cell death, limits arrhythmias, improves contractility, lengthens subject survival, or a combination thereof.

Non-limiting examples of cargo that may be used to treat myocardial infarction and/or angina include a NF-κB inhibitor, NBD peptide, hemeoxygenase, an antioxidant, iNOS, S100A1, superoxide dismutase, catalase, glutathione peroxidase, a TGFβ inhibitor, VEGF, sonic hedgehog protein, FGF-1, FGF-2, HGF, and IAPs.

The present invention provides for a method of treating a subject suffering from a metabolic defect that damages the heart comprising administering, to the subject, a therapeutically effective amount of a complex comprising a CTP linked to a cargo, where the cargo corrects the metabolic defect.

The present invention provides for a method of treating a subject suffering from Gaucher's disease comprising administering, to the subject, a therapeutically effective amount of a complex comprising a CTP linked to a glucocerebrosidase.

Where the CTP/cargo complex s administered to a subject, the subject may be a human subject or a non-human subject, such as a primate, a companion animal (eg dog, cat, horse) a laboratory animal (eg mouse, rat, rabbit or guinea pig) or a farm animal (cow, goat, etc).

The CTP/cargo complex may be administered by any route including but not limited to intravenous, intraarterial, intraperitoneal, subcutaneous, oral, rectal, etc.

The present invention provides for pharmaceutical compositions comprising CTP/cargo and a suitable pharmaceutical carrier, for example, water, physiologic saline, etc.

6. EXAMPLE 1

6.1 Materials and Methods

Phage display. A combined approach of in vitro and in vivo screening of a phage peptide display library for cardiomyocyte-specific transduction peptides was utilized. Cardiomyoblasts, H9C2 cells (ATCC, CRL-1446), were incubated with 10 (161011 pfu) of a 12-mer M13 phage peptide display library (NEB, E8110S), for 6 hours at 37° C., 5% CO2. Cells were then washed extensively, trypsinized and lysed by a single freeze-thaw cycle. Recovered phage was tittered and amplified. The post-amplified phage was again tittered and administered intravenously by retro-orbital injection at a dose of 3.561011, to a female Balb/c mouse. The mice were pre-treated with intra-peritoneal injection of Chloroquine (20 mg/Kg) 24 hours prior to and on the day of the phage injection, in order to minimize intra-lysosomal destruction of internalized phage and increase the chances of recovering internalized phage. The phage was allowed to circulate for 24 hours, after which the mice were euthanized and heart and kidney tissues obtained. The rationale for this approach was based on the observation that after intravenous injection, native M13 phage had a half-life in blood of 4.5 hours [12]. Therefore we allowed the phage to circulate for, 5-6 half-lives to maximize the chance of uptake by cardiomyocytes and minimize contamination with non-specific phage circulating in the blood stream. To minimize the destruction of internalized phage in lysosomal compartments, the mice were pre-treated with Chloroquine, a drug known to increase the pH of lysosomal compartments and theoretically decrease intracellular destruction of phage. The collected tissues were digested with collagenase and phage recovered by a single freeze/thaw cycle. Recovered phage was then tittered, normalized by tissue weight and subsequently amplified for a second round of biopanning. A total of three in vivo biopanning rounds were performed followed by sequencing of 10 plaques. All animal studies were approved by the University of Pittsburgh Institutional Animal Care and Use Committee (protocol approval number 0804422A-1).

Confocal microscopy. The cardiac targeting peptide (CTP) was synthesized in the University of Pittsburgh Peptide Synthesis Facility in either 6-carboxyfluorescene (CTP-6CF) labeled or biotinylated forms or conjugated to NBD (Nemo-binding domain), an 11-amino acid peptide (TALD-WSWLQTE; SEQ ID NO:14) which inhibits activation of the inducible NF-kB Kinase (IKK) by binding to the regulatory subunit (Nemo) of IKK. A cardiomyoblast cell line (H9C2; ATCC, CRL-1446), a mouse fibroblast cell line (NIH/3T3; ATCC, CRL-1658), a murine fibrosarcoma cell line (C57/BL6 derived fibrosarcoma MCA-205 cell line, kindly provided by P. H. Basse, Dept. of Immunology, University of Pittsburgh, Pittsburgh, Pa.), a cervical cancer cell line (HeLa; ATCC, CCL-2), and a human kidney tubular cell line (HK-2; ATCC, CRL-2190) were incubated with increasing concentrations of CTP-6CF for 30 minutes. Cells were then washed 6 times with PBS, fixed with 2% Paraformaldehyde, and counter-stained with DRAQ5 (Molecular Probes, F1303), a nuclear stain. Cells were examined by confocal fluorescent microscopy.

Luciferase assays. H9C2 cells and MCA205 cells were transfected using Lipofectamine (Invitrogen, 11668-027) with a reporter plasmid expressing luciferase under an NF-kB promoter site as well as a *Renilla* control plasmid for normalization of transfection efficiencies. Twenty-four hours later, cells were treated with increasing concentrations of CTP-NBD and 30-minutes later challenged with murine TNF-a, 10 ng/ml, for 3 hours. Cells were then washed, trypsinized, lysed and supernatant collected for Luciferase activity assay. Differences across groups were compared using an unpaired Student's t-test. A two-tailed p-value of, 0.05 was considered statistically significant.

In vivo imaging studies. The initial in vivo targeting studies were performed using CTP-6CF. Female Balb/C mice were injected retro-orbitally with CTP-6CF (25 mg/Kg) and euthanized 15 minutes later, Heart cross-sections were stained for actin using phalloidin Alexa-647 (Molecular Probes, A22287) and stained for laminin using a rabbit anti-laminin antibody followed by a goat anti-rabbit Cy3 (Jackson ImmunoResearch, 111-167-003) secondary antibody. Five non-overlapping sections were taken from each heart for quantification of green fluorescence (CTP-6CF) expressed as a percentage of total area (blue; stained for actin). A control peptide (CON; ARPLEHGSDKAT; SEQ ID NO:15), picked from the original, unselected M13 phage library, CTP and 8-Lysine (8K, a homopolymer of lysine), a known cationic protein transduction domain, were synthesized in a biotinylated form. 200 mM of biotinylated CTP, CON and 8K, or equivalent volume of PBS, were incubated with 10 ul of Streptavidin-Alexa488 (2 ng/ml; Molecular Probes, 532354) for 2 hours at room temperature. Female Balb/c mice were intravenously (retro-orbitally) injected with peptides at a dose of 10 mg/Kg and then euthanized 30 minutes post-injection. Mice were also injected with biotinylated CTP conjugated to Streptavidin-Alexa488 at a dose of 10 mg/Kg and euthanized after varying circulation times to allow for tracking studies to be performed. Post-euthanasia heart, liver, lung, spleen, kidney, skeletal muscle and brain were harvested for cryosectioning followed by confocal microscopy. Sections were cross-stained with DRAQ5, a nuclear stain. For confocal microscopy, laser intensities/gains were set using negative control (PBS injected) heart tissue to minimize background fluorescence. Once the laser intensity for FITC was set using the control hearts from PBS injected mice, it was kept constant across all subsequent imaging. Also serial scanning was performed to prevent "bleed-through" from one laser wavelength to another. Biotinylated CON or CTP peptides were labeled with neutravidin-conjugated fluospheres (Molecular Probes, F8770) with an overnight incubation at 4 uC. These fluospheres are 40 nm in diameter and fluoresce at an excitation wavelength of 605 nm, allowing for in vivo bead tracking. Female Balb/c mice received intracardiac injections of fluospheres-labeled CON peptide, CTP peptide or control PBS incubated fluospheres alone. Mice were anesthetized with isoflurane delivered by the XGI-8 Gas Anesthesia System (Xenogen). Initial isoflurane concentration was set to 2.5% and was reduced to 1.5% once the animals were anesthetized. Mice were then imaged at 30, 60, 120, and 180 minutes post-injection with the IVIS Lumina (Caliper Life Sciences Inc.). All mouse studies were approved by the Institutional Animal Care and Use Committee at the University of Pittsburgh (protocol approval number 0804422A-1).

6.2 Results

Identification of a cardiac specific transduction peptide by biopanning of a M13 phage display peptide library. In order to identify a peptide able to preferentially transduce cardiac tissue in viva, a screening protocol using a 12 amino acid peptide M13 peptide phage display library was utilized. The first cycle of screening of the phage peptide display library for cardiomyocytes specific transduction peptides was performed on a rat cardiomyocyte cell line, H9C2, in culture. The H9C2 cells were incubated with the M13 phage peptide display library then washed extensively and possibly internalized phage recovered following trypsinization and lysis by freeze-thaw. For each of the subsequent three rounds, the phage were injected intravenously and mice euthanized 24 hours post-injection. The hearts and kidneys were isolated, enyzmatically digested and associated phage recovered. The isolated phage were quantified and expressed as number of phage per gram of tissue weight. Following each round of in vivo screening, there was a steady increase in the ratio of phage recovered from the heart relative to the kidneys, suggesting enrichment of phage targeting the heart (FIG. 1). After the third round of in vivo screening, 10 plaques were selected and sequenced. Six of the 10 phage contained the identical nucleic acid sequence of gcgccgtggcatctttcgtcgcagtattctcgtact (SEQ ID NO: 17), corresponding to the peptide APWHLSSQYSRT (SEQ ID NO:1), termed cardiac targeting peptide (CTP). A BLAST search in the NCBI database revealed that this sequence shared no homology with known naturally occurring peptides or proteins. Confocal microscopy analysis demonstrates preferential targeting of cardiomyoblasts In order to examine the ability of CTP to transduce cardiomyocytes preferentially in a dose-dependent manner, fluorescent confocal microscopy was performed using the peptide coupled to 6-carboxyflouroscene (6-CF). H9C2, 3T3, MCA-205, HeLa and HK-2 cells were incubated with increasing concentrations of CTP-6-CF, washed, fixed and counterstained with DRAQ5, a nuclear stain. As shown in FIG. 2, significant internalization of CTP-6-CF was observed in H9C2 cells compared to relatively minor internalization by 3T3, MCA-205 and HeLa cells at high concentrations, with no appreciable uptake by HK-2 cells. These results, performed by confocal analysis, demonstrate both the specificity of transduction by CTP as well as that the peptide is internalized, and not simply binding to the cell membrane. Inhibition of IKK/NF-kB signal transduction by a CTP-NBD fusion peptide demonstrates functional delivery to cardiomyoblasts To confirm functional transduction of H9C2 cells by CTP, the ability to deliver a peptide, NBD, able to block activation of the IKK/NF-kB transduction pathway, was examined. H9C2 and MCA205 cells were transfected with a plasmid expressing the luciferase marker under the control of a NF-kB-dependent promoter. Twenty-four hours post-transfection, cells were pretreated with the CTP-NBD fusion peptide for 30 minutes, followed by stimulation with murine TNF-α for three hours. TNF-α treatment alone caused an increase in NF-kB transcriptional activity, which was inhibited by pretreating the H9C2 cells with increasing concentrations of CTP-NBD, in a dose-dependent fashion (FIG. 3A). In contrast, experiments performed using MCA205 cells did not show any inhibition of TNFα mediated NF-kB activation (FIG. 3B).

CTP transduces cardiac tissue in vivo. To demonstrate transduction of heart tissue in vivo, CTP-6CF or the biotinylated forms of CTP, RAN and 8K peptides coupled to Streptavidin-Alexa 488 (SA488) were injected intravenously (retro-orbitally). Mice were euthanized at varying time points and heart and multiple other organs harvested for confocal microscopy. Confocal microscopy of heart tissue from mice injected with CTP-6CF showed rapid (15 minutes) transduction of heart tissue (FIG. 4). Staining for actin and laminin showed co-localization of CTP-6CF fluorescence (green; FIG. 4A with actin (blue; FIG. 4B, but not aminin (red; FIG. 4C. These co-localization studies strongly suggest that CTP is internalized into cardiac cells in vivo, similar to the cell culture experiments. Quantification of transduction, using Metamorph software, revealed that approximately 15% of the total heart was being transduced by CTP following intravenous injection (FIG. 4E). Injection of the CTP-biotin-SA488 complex showed rapid, efficient and specific transduction of heart tissue at 30 minutes in a diffuse pattern compared to Streptavidin-Alexa 488 alone. There was no appreciable transduction seen of liver, skeletal muscle, brain (FIG. 5) or spleen. The only other organs with uptake were a small percentage of lung capillaries as well as limited transduction of endothelial cells of the glomerular capillaries in the cortex of the kidneys (FIG. 5). These results demonstrate the specificity of CTP transduction in vivo.

To examine the biodistribution of CTP-biotin-SA488 over time, mice were euthanized at different time points following intravenous injection. Even with the large CTP-biotin-SA488 complex, efficient transduction of the heart was seen at 15 minutes, mainly confined to the sub-epicardial region of the heart. At 30 minutes this became more diffuse and by 120 minutes there was almost no fluorescence seen in the heart (FIG. 6). Over these three time points, the fluorescence gradually increased in the kidney glomerular capillaries (FIG. 6, center column), suggesting that this might be the mode of excretion of this peptide or at least the fluorescence after peptide breakdown.

To confirm further the ability of CTP to transduce cardiac tissue in vivo, the peptide was coupled to fluospheres that allow for analysis of localization by whole animal imaging. Balb/c mice were injected intracardiac with 40 nm neutravidin-labeled fluospheres alone, CTP-biotin and CON-biotin labeled with these fluospheres. Mouse imaging was performed at baseline and 30, 60, 120 and 180 minutes. CTP+ fluospheres were retained in the heart, as opposed to fluospheres alone or CON+fluospheres, which dissipated immediately after injection. CTP+fluospheres could still be found localized to the heart at 3 hours post-injection (FIG. 7).

To determine the relative efficiency as well as specificity of transduction of cardiac tissue by CTP, the transduction ability of CTP was compared with 8K, a well characterized cationic protein transduction domain. Mice were injected with 10 mg/Kg dose of either CTP-SA488, 8K-SA488 or CON-SA488 conjugate and euthanized 30 minutes post-injection (FIG. 8). Mice treated with 8K-SA488 showed robust transduction of hepatocytes as well as kidney glomeruli with very little uptake in heart tissue. In contrast, CTP-SA488 conjugate showed only robust transduction of heart tissue with some uptake in the kidney glomerular capillaries and none by liver or spleen. The CON-SA488 complex did not show appreciable uptake in any organ.

It is important to note that all of the analysis of CTP transduction in vivo was performed with the L-form, the naturally occurring form, of the peptide. Preliminary experiments using a non-degradable D-form have shown a far more efficient transduction that persists for extended periods of time. Thus, it appears that there is degradation of the L-CTP complexes over time.

6.3 Discussion

The clinical application of potentially effective biological therapies for common acute cardiac conditions, like myocardial infarction, has been limited by efficiency and specificity of delivery of therapeutic agents. For example, for gene therapy approaches, such as plasmid DNA, delivery to the heart is very inefficient whereas there are significant time delays associated with cardiac gene delivery using viral-based vectors. In addition, there are issues regarding the presence of pre-existing neutralizing antibodies or immune responses to certain viral vectors. The well characterized cell penetrating peptides, like TAT from HIV coat protein, homopolymers of arginine or lysine, are not cell specific and transduce hepatocytes and multiple other organs in addition to the heart. Therefore, identifying a peptide with transduction capabilities specific for the heart would allow for new approaches for effective cardiac delivery of therapeutics.

We previously have reported the ability to identify a synovial specific transduction peptide by screening an M13 phage peptide display library for internalized phage [8]. Thus we screened a large phage peptide display library in order to identify novel peptides potentially able to transduce cardiomyocytes in vivo. Indeed, we report here the identification of a specific peptide, termed CTP, which 15 or 30 minutes post-peripheral intravenous injection can efficiently and specifically transduce cardiac tissue (FIGS. 4 and 5 respectively). Transduction of cardiomyocytes on confocal microscopy of cross-sections of the mouse heart occurred in a diffuse manner, though there appeared to be some preference for the subendocardial and subepicardial regions at earlier time point of 15 minutes. No other organ showed uptake except kidney glomeruli, limited to the cortex, and rare lung capillaries, to a much lesser extent than heart tissue. Furthermore, CTP was able to transduce heart tissue in vivo far more efficiently and in a tissue specific manner as compared to 8-Lysine, a known PTD (FIG. 7).

Since the initial description of in vivo screening of phage display libraries by Pasqualini and Ruoslahti [13], this approach has been utilized to identify peptides that target tumor vasculature [5], adipose tissue [6], pancreatic islet cells [7], synoviocytes [8], atherosclerotic plaques [9] as well as heart endothelial cells [10]. This approach also has been used in cell culture with adherent primary cardiomyocytes to isolate a 20-mer peptide with a homology to tenascin-X [11], an extracellular matrix protein. The phage displaying this peptide was found to be associated with cardiomyocytes isolated from mice treated with it in vivo. However, although it was preferentially associated with cardiomyocytes, it could still be isolated from lung tissue. Furthermore, it was unclear whether this 20-mer peptide was able to function as a cardiac transduction domain and transduce heart tissue in vivo independent of the phage carrying it.

In our screening approach, we combined a combination of cell culture and in vivo screening to identify a peptide able to be internalized into cardiac tissue. The first cycle was performed on cardiomyocytes as a screening approach to limit the population of non-specific phage from the initial phage library. All subsequent cycles were in vivo with intravenous injection in mice followed by a prolonged circulation time of 24 hours. Using this approach we identified a peptide that is able to deliver fluorescently labeled Streptavidin, a, 60 kDa complex, to cardiac cells in vivo without transduction of liver, spleen, skeletal muscle or brain, with minimal uptake by lung and glomerular capillaries. A BLAST search in the NCBI data base did not reveal homology to any known, naturally occurring proteins.

Interestingly two separate groups of investigators, using an in vitro screening of a phage display library approach, have identified the exact same sequence as CTP, and shown it to have high affinity for binding to apatite-based, bone-like minerals [14] and two specific sulfated carbohydrates [15]. However, it is unclear how the ability of CTP to interact with these cellular components in vitro facilitates transduction of cardiac specific tissue in vivo.

7. EXAMPLE 2

Viability Studies

Following the inhibition of NF-κB activation studies, we performed cell viability studies to assess changes related to peptide treatment. The experiment was repeated with H9C2 cells being doubly-transfected and pre-treated with CTP-NBD in increasing concentrations, followed by TNFα (10 ng/ml) challenge for 3 hours. After this time period, the media was aspirated and replaced with MTT assay media to assess for cell viability. As shown in FIG. 9, inhibition of NF-κB with CTP-NBD led to decrease in cell viability in a CTP-NBD dose-dependent fashion. All treatment groups were done in quadruplicate. Error bars represent 1 standard deviation (SD). These results are consistent with reports in the literature that NF-κB inhibition increases apoptosis in H9C2 cells challenged with TNFα (16), and clearly demonstrate a biological effect of the NBD peptide that is consistent with internalization of the peptide via CTP. This decrease in cell viability did not occur with TNFα treatment or CTP-NBD treatment alone.

8. EXAMPLE 3

In Vivo Studies

To demonstrate cell specificity of the CTP peptide in vivo, we undertook a second set of experiments. Balb/C, female mice were anesthetized with intra-peritoneal Avertin (2.5%, 15 μl/ gm of body weight), intubated with a 22 G cannula using direct laryngoscopy and visualization of the vocal chords, and placed on a rodent ventilator (Harvard apparatus). The chest cavity was entered using a left, lateral ternotomy approach, and an anterior infarct produced by placing a suture through the anterior wall, 2 mm inferior to the lowest dip of the left atrial appendage to blindly ligate the left anterior artery. Infarct was confirmed by the resulting pallor of the anterior wall and apex as well as wall motion abnormality produced in the region. The chest wall was closed in two layers, and the animal placed on a heating pad until awake. One week post-infarct, mice were re-anesthetized and injected intravenously with CTP-biotin-Streptavidin-Alexa488 (SA488) complex or an equivalent volume of PBS with SA488 (10 mg/Kg body weight). After 30 minutes of circulation time, hearts dissected out, mice were euthanized, washed, fixed, cryosectioned, cross-stained with DRAQ5, and confocal microscopy performed. Contiguous sections were also H&E stained to show the infarct area. FIG. 10 shows uptake of the fluorescently labeled CTP by normal heart tissue with exclusion of uptake from the infarcted, scarred myocardium (arrows). No uptake of PBS+SA488 alone was seen in any area of the heart. This experiment demonstrates in vivo cell specificity of our peptide, CTP, as it is taken up by normal myocardium and excluded from the scarred, infracted heart. The infarct is demonstrated in the H&E section by the lighter pink, thinned out area.

9. EXAMPLE 4

Human Heart Studies

Human explanted hearts were obtained from the operating rooms of UPMC at the time of ongoing heart transplants. Heart tissue was dissected from the proximal part or the base of the heart to avoid the more scarred, infarcted, distal tissue. Small 1-2 mm thick slices of heart tissue were taken and incubated with CTP-6CF (500 ul of a 1 mM solution) or PBS, for 30 and 60 mins, at 37° C./5% $CO_2$. At the end of the incubation period, the heart slices were washed in PBS 6 times, fixed in 2% paraformaldehyde for 4 hrs at room temperature, followed by 30% sucrose overnight at 4° C. Next day the tissue was frozen in liquid nitrogen-chilled isopentane and stored 58 at −80° C., for later cryosectioning, cross-staining with DRAQ5 and confocal microscopy. Confocal micrographs were obtained avoiding the edges because of the necessary damage associated with dissecting the heart tissue pieces. Confocal micrographs were taken 3-4 cell layers away from any edges. FIG. 11 demonstrates internalization of the peptide into heart myocytes.

To investigate if this transduction was indeed peptide specific, and not secondary to increased membrane leakiness resulting from tissue being ischemic, we incubated thin, 1-2 mm thick, heart slices, from a separate explanted heart, in only 6CF in PBS, CTP-6CF, RAN-6CF as well as 6CF labeled 6-Arginine, a known PTD. We also incubated heart slices with Evans blue dye (EBD) to assess for membrane leakiness. Evans blue dye fluoresces with an excitation wavelength of 620 nm and emission wavelength of 680 nm (17, 18), making it possible to be imaged with fluorescent microscopy using the appropriate lasers for excitation. Heart tissue was incubated in 500 ul of 1 mM solution of all the peptides in PBS, for 30 mins at 37° C./5% $CO_2$. At the end of the incubation period, heart slices were rinsed thoroughly 6 times in 1 ml of PBS and fixed in 2% paraformaldehyde for 4 hours, at room temperature, light-protected, followed by 30% sucrose, overnight at 4° C. The next day, tissue was frozen in liquid nitrogen chilled Isopentane, embedded in OCT, cryosectioned, cross-stained with DRAQ5, mounted and confocal microscopy performed as detailed above. Confocal microscopy showed robust and diffuse uptake of both 6R-6CF and CTP-6CF, with occasional cells showing fluorescence in RAN-treated or 6CF-treated hearts. Confocal microscopy of the EBD treated hearts did not show any fluorescence indicative of uptake which would have occurred had the membranes been significantly damaged by length of ischemia, FIG. 12 shows confocal micrographs of heart tissue treated with different peptides or controls.

The result of these ex vivo experiments demonstrates that CTP-6CF is indeed internalized by human myocytes as demonstrated by confocal microscopy and is not simply sticking to the outer surface. Moreover, this internalization is not seen with simply 6CF, the fluorescent chemical used to label all our synthesized peptides, and is not seen also with a random peptide. In contrast, 6R-6CF (homopolymer of 6 arginine amino acid residues), a known PTD, is indeed able to transducer these human myocytes ex vivo. Lastly, this internalization is not simply a result of increased membrane leakiness due to ischemia, as evidenced by lack of Evans blue dye uptake by the myocytes.

10. EXAMPLE 5

Murine Infarct Model Studies

10.1 The Model System

The following protocol was used and kept consistent from one set of experiments to another and between groups. Female, Balb/c, 10-20 week old mice were used for these set of studies. Female mice were chosen because of the ability to house 5/cage, as opposed to male mice (4/cage) and more importantly because female mice are able to tolerate cardiac insults better with lower post-operative mortality (19). Mice were anesthetized with intraperitoneal (i.p.) injection of 2.5% Avertin (a mixture of 15.5 ml tert-amyl alcohol to 25 grams of 2-2-2 Tribromoethanol-stock solution diluted to 2.5% concentration with PBS) at a dose of 15 µl/gm of body weight. Adequate anesthetic level was assessed by lack of response to toe-pinch and lack of a gag reflex. Mice were intubated, using direct visualization of the vocal chords, with a 22 G cannula and placed on a Harvard rodent ventilator apparatus. Tube placement was confirmed by symmetric expansion of the thoracic cavity. Mice were ventilated with ~0.1 cc/breath tidal volume at a rate of 110 breaths/minute.

Following successful intubation/ventilation, the chest cavity was opened using a left lateral ternotomy approach. Care was taken not to extend the surgical incision cephalad to the level of the sternal head, as a large venous confluence is present in that region and cutting through them can lead to major, exsanguinating bleed. A self-retaining mouse retractor was placed inside the incision and the teeth opened to reveal the anterior surface of the heart. The pericardium was gently removed with blunt forceps. A suture, 6-0 prolene, blue, monofilament (Owens & Minor: #8714H) was placed along the lateral wall of the left ventricle (LV), ~2 mm below the lowest dip of the left atrium and ligated with exactly 5 squarely-placed knots. Ischemia was confirmed by the resulting pallor of the myocardium and development of wall motion abnormality. The muscle layer and skin were closed in two layers with running sutures with 8-0 black, monofilament nylon suture (Owens& Minor: #2808G). The mice were extubated once spontaneous breathing was confirmed, and recovered on a heating pad. Post-operative pain was managed with subcutaneous injection of Ketoprofen, 5 mg/Kg, on post-op day 0, 1 and 2 or with subcutaneous Buprenorphine, at a dose of 0.1 mg/Kg body weight given once on the day of surgery and twice daily on post-op day 1 and 2. Mice also got one injection of subcutaneous Ampicillin, 100 mg/Kg, after surgery for prophylaxis against post-surgical infection. Right after ligation and suture placement on the anterior surface of the heart to produce myocardial infarction, and before closing the chest wall, mice received i.p. peptides in different doses. The surgeon was always blinded to the treatment. Also surgeries were carried out in a rotational fashion so that any variation due to surgical technique was distributed equally over the treatment groups.

Mice were euthanized on post-operative day 7. On day of euthanasia, mice were anesthetized, chest cavity opened, and 1 cc of 1M KCl injected via the right ventricle (RV) in order to arrest the heart in diastole to prevent contraction band necrosis. This was followed by injecting, through the right ventricle, 5 cc of Glyo-fixx (formalin-substitute), heart dissected out and placed in 15 ml of Glyo-fixx, until tissue embedded for sectioning. After paraffin embedding, cross-sections of the heart were taken starting at the apex. The first section was taken once the LV cavity appeared, with second and third sections taken 10 microns apart and cephalad of the first section. The three sections were H&E stained, light microscopy photographs taken, and area of infarct in each section mapped out using computer software Metamorph and expressed as a percent of the whole heart. The infarct area from the three sections was averaged to give the final infarct size for each mouse. All mouse protocols were approved by the University of Pittsburgh Institutional Animal Care and Use Committee (IACUC).

10.2 Infarct Studies Using 8K-NBD

First, experiments were performed to evaluate the effect, on infarct size, of suppression of NF-κB activation using the NBD peptide, with 8K as a delivery PTD, using the above murine model system. Prior to the actual infarct study, we undertook whole mouse in vivo imaging to show that 8K-NBD is able to suppress NF-κB activation in response to LPS stimulation, a known activator of NF-κB.

To demonstrate that 8K-NBD is indeed able to suppress NF-κB stimulation, we used Luciferase expressing transgenic mice with Luciferase expression controlled by an NF-κB promoter site. Mice were injected intraperitoneally (i.p.) with 8K-NBD (10 mg/Kg) at time 0 and 2 hrs with LPS injected immediately after the first 8K-NBD injection. Whole mouse in vivo imaging for Luciferase activity was performed at 30 mins, 2 hrs, 4 hrs and 6 hrs. As illustrated in FIG. 13, initial Luciferase signal was similar between the two groups of mice but at 4 and 6 hrs the signal increased in the LPS injected mice and remained stable/suppressed in the 8K-NBD treated mice.

After these initial imaging experiments, we proceeded to the infarct studies. Mice underwent left artery ligation, as detailed above, and were treated with i.p. PBS, 8K-NBD or 8K-mutant NBD (8K-mutNBD; KKKKKKKK-TTL-DASALQME; SEQ ID NO: 16), at a dose of 5 mg/Kg/injection, on post-op day 0 (immediately post-ligation) and post-op day 1 and day 2. Treatments were color-coded and administered in a rotational fashion. The surgeon was blinded to the treatment groups. Mice were euthanized on post-op day 7, heart dissected out and infarct size calculated. A record of post-op mortality was kept. Also body weight and heart weight were recorded on day of euthanasia. There was an n=6 in each group. FIG. 14 shows the post-op mortality in each of the three groups. However the heart-weight to body-weight ratios did not differ across the three groups as illustrated in FIG. 15.

As shown in FIG. 16, the infarct size were significantly different across groups and worse in mice treated with 8K-mutNBD. Mice treated with 8K-NBD had larger infarct sizes than PBS treated mice, although the difference showed a trend without reaching statistical significance.

A cross-section from each heart was taken and apoptosis assessed by TUNEL staining. The nuclei were stained with Dapi, and the number of TUNEL positive nuclei expressed as a percentage of total nuclei in each field. The whole heart cross-section was taken into consideration by taking 5-6 contiguous, non-overlapping sections from each heart. FIG. 17 demonstrates that the highest number of apoptotic nuclei occurred in 8K-NBD treated hearts, followed by 8K-mut-NMD hearts with least number seen in the PBS treated heart sections. FIG. 18 illustrates the TUNEL staining data in a quantitative manner.

From these set of experiments we conclude that although 8K-NBD is able to inhibit NF-κB activation in response to LPS stimulation, this inhibition in a mouse infarct model appears to be detrimental and results in increased apoptosis occurring, as assessed by TUNEL staining, and a larger infarct size. Although 8K-mutNBD had lesser number of apoptotic nuclei, the infarct size was actually larger. This difference from the PBS treated group reached statistical significance. It is possible that although 8K-mutNBD has much reduced NF-κB inhibitory activity, it still has some level of inhibition which in an acute infarct model is detrimental. The apoptosis being less with a larger infarct size is difficult to explain and possibly within the realm of biological variability as the infarct size in 8K-NBD treated and 8K-mut-NBD treated mice was not statistically significant.

10.3 Infarct Studies Using CTP-NBD

Female, Balb/c mice underwent left artery ligation as detailed above. Mice were treated either with PBS, CTP- NBD or 8K-NBD (both at a dose of 10 mg/Kg body weight) on day of surgery, delivered i.p., right after ischemia was confirmed. Peptides were suspended in PBS. The surgeon was blinded to the treatment allocation and treatment was given in a rotational fashion. Post-operative pain control was achieved with I/M Ketoprofen (5 mg/Kg) on day 0, 1 and 2. Mice were euthanized on post-op day 7, heart dissected and processed for infarct size determination as detailed above. The post-operative mortality in each group is shown in FIG. 19.

The infarct size is shown in FIG. 20. As before, the infarct size was slightly more in the 8K-NBD treated group compared to the PBS treated group. However the CTP-NBD treated group showed a trend towards smaller infarct sizes.

10.4 D-Isoform Infarct Studies

The D-isoform of CTP-NBD was synthesized in the University of Pittsburgh Peptide Synthesis Facility, with a fraction biotinylated at the C-terminus for conjugation with Streptavidin-Alexa488 (SA488) for tracking studies. Two hundred microliters of a 1 mM solution of D-CTP-NBD, biotinylated form, was incubated with 20 ul of SA488 (2 mg/ml stock solution) at room temperature (RT), light-protected for 60 minutes. 1 ml of PBS was also incubated with 20 ul of SA488 under identical incubation conditions. Female, Balb/c mice were anesthetized with i.p. Avertin and injected retro-orbitally with the D-CTP-NBD-SA488 complex at a dose of 10 mg/Kg or PBS+SA488. Mice were then euthanized at 30 minutes (time to peak transduction with L-isoform CTP) or 120 minutes, hearts taken, fixed in 2% paraformaldehyde at RT for 4 hrs, overnight 30% Sucrose at 4° C., frozen in liquid N2 chilled Isopentane and cryosectioned. PBS injected mice were euthanized at only 30 minutes. After cross-staining with DRAQ5, a nuclear stain, confocal microscopy was performed to look for fluorescence. Confocal microscopy showed robust uptake of D-CTP-NBD-SA488 complex albeit at a slower rate than L-isoform CTP. There was beginning of transduction noted at the edges with deeper tissue showing transduction at 120 minutes, as shown in FIG. 21.

To investigate if D-CTP-NBD retains its ability to inhibit NF-κB activation in response to TNFα stimulation, the cell culture Luciferase studies were repeated. H9C2 cells were plated onto 96-well plates and double transfected with a plasmid carrying Luciferase under an NF-κB promoter site as well as a *Renilla* expressing control plasmid. 24 hours post transfection, cells were pre-treated with increasing concentrations of the D-CTP-NBD peptide and 30 minutes later challenged with TNFα for 3 hours. After three hours, cells were washed, trypsinized, lysed and Luciferase and *Renilla* activity quantified in a luminometer. All work was done in quadruplicate. FIG. 22 shows that D-CTP-NBD is a less potent inhibitor of NF-κB activation with any appreciable inhibition occurring only at the highest tested dose (400 uM).

Although inhibition of NF-κB did occur, it was seen only at the highest tested dose. Given that the transduction process was slowed down as seen in the in vivo imaging mouse study (FIG. 21), we hypothesized that perhaps 30 mins of incubation/lead time was not adequate with D-CTP-NBD. However pre-incubating with 60 mins or 120 mins produced identical results with ~40% inhibition seen, only with the highest dose (400 μM), as compared with the TNFα-stimulated cells (results not shown).

To study the effect of D-CTP-NBD on infarcts, mice underwent left artery ligation, as detailed above. Only one dose of D-CTP-NBD or PBS was administered at time of surgery (5 mg/Kg, i.p.), and mice were euthanized on post-op day 7. The surgeon was blinded to the treatment allocation and post-op pain control was achieved with s.q. Buprenorphine (0.1 mg/Kg body weight). As shown in FIG. 23, infarct size did not differ between the two groups. In addition, if infarct sizes of less than 10% were excluded, the mean infarct size in the two groups was nearly identical leading us to conclude that treatment with D-CTP-NBD did not have any significant effect on infarct size. Probably the most likely explanation for this lack of an effect, despite promising earlier data, is the lack of adequate inhibition of NF-κB activation by the D-isoform of NBD. Although inhibition in cell culture studies, utilizing H9C2 cells, did occur, it was apparent only at the highest dose tested (400 μM). This level might not have been achievable at the dose of 10 mg/Kg body weight in vivo to produce a biological effect. In addition, later studies of NF-κB inhibition (20-22) have shown that infarct sizes are similar in control and NF-κB inhibited mice, but remodeling is favorably affected in the latter group. In our studies, mice were euthanized at post-op day 7, which would be too early to see differences in post-infarct modeling or differences in left ventricular function.

11. References

1. Wiviott S D, Morrow D A, Frederick P D, Giugliano R P, Gibson C M, et al. (2004) Performance of the thrombolysis in myocardial infarction risk index in the National Registry of Myocardial Infarction-3 and -4: a simple index that predicts mortality in ST-segment elevation myocardial infarction. J Am Coll Cardiol 44:783-9,
2. Rogers W J, Canto J G, Lambrew C T, Tiefenbrunn A J, Kinkaid B, et al. (2000) Temporal trends in the treatment of over 1.5 million patients with myocardial infarction in the US from 1990 through 1999: the National Registry of Myocardial Infarction 1, 2 and 3. J Am Coll Cardiol 36(7): 2056-63.
3. Pachori A S, Melo L G, Hart M L, Noiseux N, Zhang L, et al. (2004) Hypoxiaregulated therapeutic gene as a preemptive treatment strategy against ischemial reperfusion tissue injury. Proc Natl Acad Sci USA 101(33): 12282-7.
4. Kawano 5, Kubota T, Monden Y, Tsutsumi T, Inoue T, et al. (2006) Blockade of NF-kappaB improves cardiac function and survival after myocardial infarction. Am J Physiol Heart Circ Physiol 291(3): H1337-44,
5. Arap W, Pasqualini R, Ruoslahti E (1998) Cancer treatment by targeted drug delivery to tumor vasculature in a mouse model. Science 279(5349): 377-80.
6. Kolonin M G, Saha P K, Chan L, Pasqualini R, Arap W (2004) Reversal of obesity by targeted ablation of adipose tissue. Nat Med 10(6): 625-32.
7. Yao V J, Ozawa M G, Trepel M, Arap W, McDonald D M, et al. (2005) Targeting pancreatic islets with phage display assisted by laser pressure catapult microdissection. Am J Pathol 166(2): 625-36.
8. Mi Z, Lu X, Mai J C, Ng B G, Wang G, et al. (2003) Identification of a synovial fibroblast-specific protein transduction domain for delivery of apoptotic agents to hyperplastic synovium. Mol Ther 8(2): 295-305.
9. Kelly K A, Nahrendorf M, Yu A M, Reynolds F, Weissleder R (2006) In vivo phage display selection yields atherosclerotic plaque targeted peptides for imaging. Mol Imaging Biol 8(4): 201-7.

10. Zhang L, Hoffman J A, Ruoslahti E (2005) Molecular profiling of heart endothelial cells. Circulation 112(11): 1601-11.
11. McGuire M J, Samli K N, Johnston S A, Brown K C (2004) In vitro selection of a peptide with high selectivity for cardiomyocytes in vivo. J Mol Biol 342(1): 171-82.
12. Molenaar T J, Michon I, de Haas S A, van Berkel T J, Kuiper J (2002) Uptake and processing of modified bacteriophage M13 in mice: implications for phage display. Virology 293(1): 182-91.
13. Pasqualini R, Ruoslahti E (1996) Organ targeting in vivo using phage display peptide libraries. Nature 380 (6572): 364-6.
14. Segvich S J, Smith H C, Kohn D H (2009) The adsorption of preferential binding peptides to apatite-based materials. Biomaterials 30(7): 1287-98.
15. Hyun S, Lee E H, Park J, Yu J (2008) Tentacle type peptides as artificial lectins against sulfated Lewis X and A. Bioorg Med Chem Lett 18(14): 4011-4.
16. Bergmann, M. W., et al., Effect of NF-kappa B Inhibition on TNF-alpha-induced apoptosis and downstream pathways in cardiomyocytes. J Mol Cell Cardiol, 2001. 33(6): p. 1223-32.
17. del Valle, J., et al., A new method for determining blood-brain barrier integrity based on intracardiac perfusion of an Evans Blue-Hoechst cocktail. J Neurosci Methods, 2008. 174(1): p. 42-9.
18. Rakos, G., et al., Evans Blue fluorescence permits the rapid visualization of non-intact cells in the perilesional rim of cold-injured rat brain. Acta Neurobiol Exp (Wars), 2007. 67(2): p. 149-54.
19. Cavasin, M. A., et al., Gender differences in cardiac function during early remodeling after acute myocardial infarction in mice. Life Sci, 2004. 75(18): p. 2181-92.
20. Kawano, S., et al., Blockade of NF-kappaB improves cardiac function and survival after myocardial infarction. Am J Physiol Heart Circ Physiol, 2006. 291(3): p. H1337-44,
21. Wakatsuki, S., et al., A novel IKK inhibitor suppresses heart failure and chronic remodeling after myocardial ischemia via MMP alteration. Expert Opin Ther Targets, 2008. 12(12): p. 1469-76.
22. Frantz, S., et al., Absence of NF-kappaB subunit p50 improves heart failure after myocardial infarction. FASEB J, 2006. 20(11): p. 1918-20.
23. Melo L G, Agrawal R, Zhang L, Rezvani M, Mangi A A, Ehsan A, Griese D P, Dell'Acqua G, Mann M J, Oyama J, Yet S F, Layne M D, Perrella M A, Dzau V J. Gene therapy strategy for long-term myocardial protection using adeno-associated virus-mediated delivery of heme oxygenase gene. Circulation. 2002 Feb. 5; 105(5): 602-7.
24. Li Q, Guo Y, Tan W, et al., Gene therapy with iNOS provides long-term protection against myocardial infarction without adverse functional consequences. AJP-Heart Feb. 2006 vol. 290 no. 2 H584-H589.
25. Pleger S T, Remppis A, Heidt B, et al., S100A1 Gene Therapy Preserves in Vivo Cardiac Function after Myocardial Infarction. Molecular Therapy (2005) 12, 1120-1129.
26. Li Q, Bolli R, Qiu Y, et al. Gene Therapy With Extracellular Superoxide Dismutase Protects Conscious Rabbits Against Myocardial Infarction. Circulation. 2001; 103:1893-1898.
27. U.S. Ser. No. 09/988,910 by Brent A. French, United States Patent Application Publ. 2002 0061299.
28. Okada H, Takemura G, Kosai K, et al. Postinfarction Gene Therapy Against Transforming Growth Factor-β Signal Modulates Infarct Tissue Dynamics and Attenuates Left Ventricular Remodeling and Heart Failure. Circulation. 2005; 111: 2430-2437
29. Whitten M G, Reiss R, Choi D, et al. 31st Annual Meeting Abstracts, Western Thoracic Surgical Association, Jun. 22-25, 2005.
30. Jiang Z S, Padua R R, Ju H, Doble B W, Jin Y, Hao J, Cattini P A, Dixon I M, Kardami E., Acute protection of ischemic heart by FGF-2: involvement of FGF-2 receptors and protein kinase C. Am J Physiol Heart Circ Physiol. 2002 March; 282(3):H1071-80.
31. Htun P, Ito W D, Hoefer I E, Schaper J, Schaper W. Intramyocardial infusion of FGF-1 mimics ischemic preconditioning in pig myocardium. J Mol Cell Cardiol. 1998 Apr.; 30(4):867-77.
32. Roncalli J, Renault M A, Tongers J, et al., Sonic Hedgehog-Induced Functional Recovery After Myocardial Infarction Is Enhanced by AMD3100-Mediated Progenitor-Cell Mobilization. J Am Coll Cardiol, 2011; 57:2444-2452.
33. Segvich S, Biswas S, Becker U et al., Identification of peptides with targeted adhesion to bone-like mineral via phage display and computational modeling. Cells Tissues Organs 2009, 189(1-4):245-251.
34. Lu s, Xu X, Zhao W, et al., Targeting of embryonic stem cells by peptide-conjugated quantum dots. PloS ONE 2010, 5(8):e12075.
35. Internation Patent Application Publication No. WO2011/049449, PCT/NL2010/050700.
36. United States Patent Application Publication No. 2010/0310495, U.S. Ser. No. 12/785,694 by Schneider et al.

Various publications are cited herein, the contents of which are hereby incorporated by reference in their entireties.

We claim:

1. A method of introducing a cargo into a cardiac muscle cell comprising administering, to the cardiac muscle cell, an amount of a complex comprising a cardiac targeting peptide linked to a cargo effective to introduce the cargo into the muscle cell, wherein the cardiac targeting peptide comprises the sequence APWHLSSQYSRT (SEQ ID NO:1).

2. The method of claim 1, wherein the cargo comprises a radioisotope, fluorescent marker, gadolinium marker, luciferase marker, microsphere or nanoparticle.

3. A method of introducing a cargo into a cardiac muscle cell comprising administering, to the cardiac muscle cell, an amount of a complex comprising a cardiac targeting peptide linked to a cargo effective to introduce the cargo into the muscle cell, wherein the cardiac targeting peptide
(a) is between 8 and 12 amino acids in length and comprises the sequence HLSSQYSR (SEQ ID NO:2), with the proviso that when the cardiac targeting peptide is 12 amino acids in length it is APWHLSSQX$_1$SRT (SEQ ID NO:7) where X$_1$ is W; or
(b) is between 8 and 12 amino acids in length and comprises the sequence HLSSQYSR (SEQ ID NO:2) in which one amino acid of HLSSQYSR (SEQ ID NO:2) is either deleted or substituted by another amino acid.

4. The method of claim 3, wherein the cardiac targeting peptide is selected from the group consisting of:

```
APWHLSSQYSR;                    (SEQ ID NO: 3)

PWHLSSQYSRT;                    (SEQ ID NO: 4)

PWHLSSQYSR;                     (SEQ ID NO: 5)

APWHLSSQ X₁SRT                  (SEQ ID NO: 7)
where X₁ is W;

PX₁HLSSQYSRT                    (SEQ ID NO: 8)
where X₁ is W or Y;

PWHLSSQ X₁SRT                   (SEQ ID NO: 9)
where X₁ is W or Y;

X₁HLSSQYSRT                     (SEQ ID NO: 10)
where X₁ is W or Y;

WHLSSQ X₁SRT                    (SEQ ID NO: 11)
where X₁ is W or Y;

X₁HLSSQYSR                      (SEQ ID NO: 12)
where X₁ is W or Y;
and

WHLSSQ X₁SR                     (SEQ ID NO: 13)
where X₁ is W or Y.
```

5. The method of claim 3, wherein the cargo comprises a radioisotope, fluorescent marker, gadolinium marker, luciferase marker, microsphere or nanoparticle.

6. A method of treating a human subject suffering from a myocardial infarction, comprising introducing a cargo into a cardiac muscle cell of the human subject comprising administering, to the human subject, a therapeutically effective amount of a complex comprising a cardiac targeting peptide linked to a cargo, where the cargo inhibits cell death, inhibits arrhythmias, improves contractility, lengthens subject survival, or a combination thereof, wherein the cardiac targeting peptide
(a) is between 8 and 12 amino acids in length and comprises the sequence HLSSQYSR (SEQ ID NO:2), with the proviso that when the cardiac targeting peptide is 12 amino acids in length it is selected from the group consisting of APX$_1$HLSSQYSRT (SEQ ID NO:6) where X$_1$ is Y, and APWHLSSQX$_1$SRT (SEQ ID NO:7) where X$_1$ is W; or
(b) is between 8 and 12 amino acids in length and comprises the sequence HLSSQYSR (SEQ ID NO:2) in which one amino acid of HLSSQYSR (SEQ ID NO:2) is either deleted or substituted by another amino acid.

7. The method of claim 6 where the cargo is selected from an NF-κB inhibitor, NSD peptide, hemeoxygenase, an antioxidant, iNOS, S100A1, superoxide dismutase, catalase, glutathione peroxidase, a TGFβ inhibitor, VEGF, FGF-1, FGF-2, sonic hedgehog protein, HGF and an IAP.

8. The method of claim 6, wherein the cardiac targeting peptide is selected from the group consisting of:

```
APWHLSSQYSR;                    (SEQ ID NO: 3)

PWHLSSQYSRT;                    (SEQ ID NO: 4)

PWHLSSQYSR;                     (SEQ ID NO: 5)

APWHLSSQ X₁SRT                  (SEQ ID NO: 7)
where X₁ is W;
```

```
PX₁HLSSQYSRT            (SEQ ID NO: 8)
where X₁ is W or Y;

PWHLSSQ X₁SRT           (SEQ ID NO: 9)
where X₁ is W or Y;

X₁HLSSQYSRT             (SEQ ID NO: 10)
where X₁ is W or Y;

WHLSSQ X₁SRT            (SEQ ID NO: 11)
where X₁ is W or Y;

X₁HLSSQYSR              (SEQ ID NO: 12)
where X₁ is W or Y;
and

WHLSSQ X₁SR             (SEQ ID NO: 13)
where X₁ is W or Y.
```

9. A method of treating a human subject suffering from a myocardial infarction, comprising introducing a cargo into a cardiac muscle cell of the human subject comprising administering, to the human subject, a therapeutically effective amount of a complex comprising a cardiac targeting peptide linked to a cargo, where the cargo inhibits cell death, inhibits arrhythmias, improves contractility, lengthens subject survival, or a combination thereof, where the cardiac targeting peptide has the sequence APWHLSSQYSRT (SEQ ID NO:1).

10. The method of claim 9 where the cargo is selected from an NF-κB inhibitor, NBD peptide, hemeoxygenase, an antioxidant, iNOS, S100A1, superoxide dismutase, catalase, glutathione peroxidase, a TGFβ inhibitor, VEGF, FGF-1, FGF-2, sonic hedgehog protein, HGF and an IAP.

11. A method of treating a subject suffering from a metabolic defect that damages the heart comprising introducing a cargo into a cardiac muscle cell of the human subject comprising administering, to the subject, a therapeutically effective amount of a complex comprising a cardiac targeting peptide linked to a cargo, where the cargo corrects the metabolic defect,
wherein the cardiac targeting peptide
(a) is between 8 and 12 amino acids in length and comprises the sequence HLSSQYSR (SEQ ID NO:2), with the proviso that when the cardiac targeting peptide is 12 amino acids in length it is selected from the group consisting of APX₁HLSSQYSRT (SEQ ID NO:6) where X₁ is Y, and APWHLSSQX₁SRT (SEQ ID NO:7) where X₁ is W; or
(b) is between 8 and 12 amino acids in length and comprises the sequence HLSSQYSR (SEQ ID NO:2) in which one amino acid of HLSSQYSR (SEQ ID NO:2) is either deleted or substituted by another amino acid.

12. The method of claim 11, where the metabolic defect is Gaucher's disease and the cargo is glucocerebrosidase.

13. The method of claim 11, wherein the cardiac targeting peptide is selected from the group consisting of:

```
APWHLSSQYSR;            (SEQ ID NO: 3)

PWHLSSQYSRT;            (SEQ ID NO: 4)

PWHLSSQYSR;             (SEQ ID NO: 5)

APWHLSSQ X₁SRT          (SEQ ID NO: 7)
where X₁ is W;

PX₁HLSSQYSRT            (SEQ ID NO: 8)
where X₁ is W or Y;

PWHLSSQ X₁SRT           (SEQ ID NO: 9)
where X₁ is W or Y;

X₁HLSSQYSRT             (SEQ ID NO: 10)
where X₁ is W or Y;

WHLSSQ X₁SRT            (SEQ ID NO: 11)
where X₁ is W or Y;

X₁HLSSQYSR              (SEQ ID NO: 12)
where X₁ is W or Y;
and

WHLSSQ X₁SR             (SEQ ID NO: 13)
where X₁ is W or Y.
```

14. A method of treating a subject suffering from a metabolic defect that damages the heart comprising introducing a cargo into a cardiac muscle cell of the human subject comprising administering, to the subject, a therapeutically effective amount of a complex comprising a cardiac targeting peptide linked to a cargo, where the cargo corrects the metabolic defect, where the cardiac targeting peptide has the sequence APWHLSSQYSRT (SEQ ID NO:1).

15. The method of claim 14, where the metabolic defect is Gaucher's disease and the cargo is glucocerebrosidase.

16. A method of introducing a detectable cargo into a cardiac muscle cell comprising administering, to the cardiac muscle cell, an amount of a complex comprising a cardiac targeting peptide linked to a cargo effective to introduce the cargo into the muscle cell, wherein the cardiac targeting peptide comprises the sequence APWHLSSQYSRT (SEQ ID NO:1), and wherein the cargo comprises a detectable compound.

17. The method of claim 16, wherein the detectable compound comprises a detectable radioisotope, fluorescent marker, gadolinium marker, or luciferase marker.

18. A method of introducing a detectable cargo into a cardiac muscle cell comprising administering, to the cardiac muscle cell, an amount of a complex comprising a cardiac targeting peptide linked to a cargo effective to introduce the cargo into the muscle cell,
wherein the cardiac targeting peptide
(a) is between 8 and 12 amino acids in length and comprises the sequence HLSSQYSR (SEQ ID NO:2), with the proviso that when the cardiac targeting peptide is 12 amino acids in length it is APWHLSSQX₁SRT (SEQ ID NO:7) where X₁ is W; or
(b) is between 8 and 12 amino acids in length and comprises the sequence HLSSQYSR (SEQ ID NO:2) in which one amino acid of HLSSQYSR (SEQ ID NO:2) is either deleted or substituted by another amino acid, and wherein the cargo comprises a detectable compound.

19. The method of claim 18, wherein the detectable compound comprises a detectable radioisotope, fluorescent marker, gadolinium marker, or luciferase marker.

* * * * *

SEQUENCE LISTING

<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ala Pro Trp His Leu Ser Ser Gln Tyr Ser Arg Thr
1               5                   10

```
<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Leu Ser Ser Gln Tyr Ser Arg
1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Pro Trp His Leu Ser Ser Gln Tyr Ser Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Trp His Leu Ser Ser Gln Tyr Ser Arg Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Trp His Leu Ser Ser Gln Tyr Ser Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp or Tyr

<400> SEQUENCE: 6

Ala Pro Xaa His Leu Ser Ser Gln Tyr Ser Arg Thr
1               5                   10

<210> SEQ ID NO 7
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Trp or Tyr

<400> SEQUENCE: 7

Ala Pro Trp His Leu Ser Ser Gln Xaa Ser Arg Thr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Trp or Tyr

<400> SEQUENCE: 8

Pro Xaa His Leu Ser Ser Gln Tyr Ser Arg Thr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Trp or Tyr

<400> SEQUENCE: 9

Pro Trp His Leu Ser Ser Gln Xaa Ser Arg Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or Tyr

<400> SEQUENCE: 10

Xaa His Leu Ser Ser Gln Tyr Ser Arg Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Trp or Tyr
```

<400> SEQUENCE: 11

Trp His Leu Ser Ser Gln Xaa Ser Arg Thr
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp or Tyr

<400> SEQUENCE: 12

Xaa His Leu Ser Ser Gln Tyr Ser Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Trp or Tyr

<400> SEQUENCE: 13

Trp His Leu Ser Ser Gln Xaa Ser Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ala Leu Asp Trp Ser Trp Leu Gln Thr Glu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Pro Leu Glu His Gly Ser Asp Lys Ala Thr
1               5                   10

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Lys Lys Lys Lys Lys Lys Lys Lys Thr Thr Leu Asp Ala Ser Ala Leu
1               5                   10                  15

Gln Met Glu

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcgccgtggc atctttcgtc gcagtattct cgtact                              36
```